United States Patent [19]

Stemmer

[11] Patent Number: 5,512,463

[45] Date of Patent: * Apr. 30, 1996

[54] ENZYMATIC INVERSE POLYMERASE CHAIN REACTION LIBRARY MUTAGENESIS

[75] Inventor: Willem P. C. Stemmer, Carlsbad, Calif.

[73] Assignee: Eli Lilly and Company, Indianapolis, Ind.

[*] Notice: The portion of the term of this patent subsequent to Jan. 19, 2014, has been disclaimed.

[21] Appl. No.: 252,057

[22] Filed: Jun. 1, 1994

Related U.S. Application Data

[63] Continuation of Ser. No. 806,154, Dec. 12, 1991, abandoned, which is a continuation-in-part of Ser. No. 691,140, Apr. 26, 1991, abandoned.

[51] Int. Cl.$^6$ .......................... C12P 19/34; C12P 21/00; C07H 21/04; C12Q 1/68
[52] U.S. Cl. .................... 435/91.2; 435/69.1; 435/6; 536/24.1; 536/24.33; 935/77; 935/78
[58] Field of Search .......................... 435/6, 91.2, 69.1; 530/326; 536/24.33, 24.1, 23.1

[56] References Cited

U.S. PATENT DOCUMENTS

| | | | |
|---|---|---|---|
| 4,800,159 | 1/1989 | Mullis et al. | 435/91.2 |
| 4,935,357 | 6/1990 | Szybalski | 435/91.2 |
| 4,959,312 | 9/1990 | Sirotkin | 435/91.1 |
| 5,023,171 | 6/1991 | Ho et al. | 435/6 |

FOREIGN PATENT DOCUMENTS 0414134  2/1991  European Pat. Off. .

OTHER PUBLICATIONS

Hermes, et al. "Searching Sequence Space by Definably Random Mutagenesis: Improving the Catalytic Potency of an Enzyme": Proc. Natl. Acad. Sci. 87: 696–700 (1990).
Higuchi, et al. "A General Method of in vitro Preparation and Specific Mutagenesis of DNA Fragment: Study of Protein and DNA Interactions" Nucl. Acids Res. 16(15): 7351–7367 (1988).
Jones, et al. "A Rapid Method for Site–Specific Mutagenesis and Directional Subcloning by Using the Polymerase Chain Reaction to Generate Recombinant Circles" BioTechniques 8: 178–183 (1990).
Jones, et al. "A Rapid Method for Recombination and Site–Specific Mutagenesis by Placing Homologous Ends in DNA Using Polymerase Chain Reaction" BioTechniques 10: 62–66 (1991).

(List continued on next page.)

*Primary Examiner*—W. Gary Jones
*Assistant Examiner*—Lisa Arthur
*Attorney, Agent, or Firm*—Knobbe, Martens, Olson & Bear

[57] ABSTRACT

This invention discloses a method for generating a recombinant library by introducing one or more changes within a predetermined region of double-stranded nucleic acid, comprising providing a first primer population and a second primer population, each of the populations having a variable base composition at known positions along the primers, the primers incorporating a class IIS restriction enzyme recognition sequence, being capable of directing change in the nucleic acid sequence and being substantially complementary to the double stranded nucleic acid to permit hybridization thereto. The method additionally comprises hybridizing the first and second primer populations to opposite strands of the double stranded nucleic acid to form a first pair of primer-templates oriented in opposite directions, performing enzymatic inverse polymerase chain reaction to generate at least one linear copy of the double stranded nucleic acid incorporating the change directed by the primers, cutting the double stranded nucleic acid copy with a class IIS restriction enzyme to form a restricted linear nucleic acid molecule containing the change, joining termini of the restricted linear nucleic acid molecule to produce double-stranded circular nucleic acid and introducing the nucleic acid into compatible host cells. A method is additionally provided for generating a recombinant library using wobble-base mutagenesis.

27 Claims, 7 Drawing Sheets

OTHER PUBLICATIONS

Kozak, M. "Compilation and Analysis of Sequences Upstream from the Translational Start Site in Eukaryotic mRNAs": Nucl. Acids Res. 12(2): 857–872 (1984).

Movva, et al. "Amino Acid Sequence of the Signal Peptide of ompA Protein, a Major Outer Membrane Protein of *Escherichia coli*" J. of Biol. Chem. 255: 27–29 (1980).

Movva, et al. "Gene Structure of the OmpA Protein, a Major Surface Protein of *Escherichia coli* Required for Cell—Cell Interaction" J. Mol. Biol. 143: 317–328 (1980).

Nelson, et al. "A General Method of Site–Specific Mutagenesis Using a Modification of the *Thermus aquaticus* Polymerase Chain Reaction" Anal. Biochem. 180: 147–151 (1989).

Saiki, et al. "Primer–Directed Enzymatic Amplification of DNA with a Thermostable DNA Polymerase" Science 239: 487–491 (1988).

Seed, B. "Purification of Genomic Sequence from Bacteriophase Libraries by Recombination and Selection in vivo" Nucl. Acids Res. 11(8): 2427–2455 (1983).

Skerra, et al. "Filter Screening of Antibody Fab Fragments Secreted from Individual Bacterial Colonies: Specific Detection of Antigen Binding with a Two–Membrane System" Anal. Biochem. 196:151–155 (1991).

Stemmer and Morris, "Enzymatic Inverse PCR: A Restriction Site Independent Single–Fragment Method for High–Efficiency, Site–Directed Mutagenesis" BioTechniques 13(2): 216–200 (1992).

Jones, et al., "DNA Mutagenesis and Recombination" Nature 344: 793–794 (Apr. 1990).

Huang, et al., Vectors: A survey of Molecular Cloning Vectors and teir uses (1987) R. L. Rodriquez and D. T. Denhardt (eds.) Buttenworth Publ. pp. 269–283.

Szardenings et al. (1990) Gene, vol. 94, pp. 1–7.

Hermes, J. D. et al. (1989) Gene, vol. 84, pp. 143–151.

Tomic et al. (1990) Nucleic Acids Research, vol. 18, No. 6, pp. 1656.

Hemsley, A. et al. (1989) Nucleic Acids Research, vol. 17, No. 16, pp. 6545–6551.

Bucheler et al. (1990) Gene, vol. 96, pp. 271–276.

CLASS 2S RESTRICTION ENZYMES SUITABLE FOR USE WITH EIPCR

| Enzyme | Recognition Sequence |
|---|---|
| Bsa1 | GGTCTCN|NNNN |
| Bbs1 | GAAGACNN|NNNN |
| Ear1 | CTCTTCN|NNN |
| Bsm1 | GAATGCN| |
| BspM1 | ACCTGCNNNN|NNNN |
| Alw1 | GGATCNNNN|N |
| BsmA1 | GTCTCN|NNNN |
| Bsr1 | ACTGG|N |
| Fok1 | GGATGNNNNNNNNN|NNNN |
| Hga1 | GACGCNNNNN|NNNNN |
| Hph1 | GGTGANNNNNNN|N |
| Mbo2 | GAAGANNNNNNN|N |
| Ple1 | GAGTCNNNN|N |
| SfaN1 | GCATCNNNNN|NNNN |
| Mnl1 | CCTCNNNNNNN| |

Fig. 3

ENZYMATIC INVERSE POLYMERASE CHAIN REACTION LIBRARY MUTAGENESIS

This application is a file wrapper continuation of U.S. patent application Ser. No. 806,154, filed Dec. 12, 1991, which is now abandoned, which was a continuation-in-part of U.S. patent application Ser. No. 691,140, filed Apr. 26, 1991, which is now abandoned.

FIELD OF THE INVENTION

These inventions relate generally to the amplification of DNA sequences by polymerase chain reaction (PCR) and, more particularly, to the alteration of DNA sequences using PCR.

BACKGROUND OF THE INVENTION

Recombinant DNA techniques have revolutionized molecular biology and genetics by permitting the isolation and characterization of specific DNA fragments. Of major impact has been the exponential amplification of small amounts of DNA by a technique known as the polymerase chain reaction (PCR). The sensitivity, speed and versatility of PCR makes this technique amenable to a wide variety of applications such as medical diagnostics, human genetics, forensic science and other disciplines of the biological sciences.

PCR is based on the enzymatic amplification of a DNA sequence that is flanked by two oligonucleotide primers which hybridize to opposite strands of the target sequence. The primers are oriented in opposite directions with their 3' ends pointing towards each other. Repeated cycles of heat denaturation of the template, annealing of the primers to their complementary sequences and extension of the annealed primers with a DNA polymerase result in the amplification of the segment defined by the 5' ends of the PCR primers. Since the extension product of each primer can serve as a template for the other primer, each cycle results in the exponential accumulation of the specific target fragment, up to several million fold in a few hours. The method can be used with a complex template such as genomic DNA and can amplify a single-copy gene contained therein. It is also capable of amplifying a single molecule of target DNA in a complex mixture of RNAs or DNAs and can, under some conditions, produce fragments up to ten kb long. The PCR technology is the subject matter of U.S. Pat. Nos. 4,683,195, 4,800,159, 4,754,065, and 4,683,202 all of which are incorporated herein by reference.

In addition to the use of PCR for amplifying target sequences, this method has also been used to generate site-specific mutations in known sequences. Mutations are created by introducing mismatches into the oligonucleotide primers used in the PCR amplification. The oligonucleotides, with their mutant sequences, are then incorporated at both ends of the linear PCR product. In addition to their mutated sequences, the primers often contain restriction enzyme recognition sequences which are used for subcloning the mutated linear DNAs into vectors in place of the wild type sequences. Although this procedure is relatively simple to perform, its applications are limited because appropriate restriction sequences are not always conveniently located for substituting the mutant sequence with the wild-type sequence. Restriction sequences can be incorporated into the wild-type sequences for subcloning. However, such extraneous sequences can cause detrimental effects to the function of the gene or resulting gene product. Moreover, PCR products typically contain heterogeneous termini resulting from the addition of extra nucleotides and/or incomplete extension of the primer-templates. Such termini are extremely difficult to ligate and therefore result in a low subcloning efficiency.

Several modifications of the PCR-based site-directed mutagenesis strategies have been developed to circumvent such limitations, but they too have undesirable features. The most prominent undesirable feature exhibited by these alternative methods is a low frequency of correct mutations. For example, inverse PCR (IPCR) is a method which amplifies a circular plasmid rather than a linear molecule, Hemsley et al., Nuc. Acid. Res. 17:6545–6551 (1989), which is incorporated herein by reference. In this technique, two primers which are located back to back on opposing DNA strands of a plasmid drive the PCR reaction. The resultant PCR product, a linear DNA molecule identical in length to the starting plasmid, contains any mutations which were designed into the primers. The product is then enzymatically prepared for ligation by blunting and phosphorylating the termini. Enzymatic treatment of the termini is a necessary step for ligation due to heterogeneous termini associated with PCR products. These treatments are likely to be incomplete and cause unwanted mutations as well as result in a low ligation and transformation efficiency due to the additional required steps.

Recombinant circle PCR (RCPCR), Jones and Howard, BioTechniques 8:178–183 (1990), and recombination PCR (RPCR), Jones and Howard, BioTechniques 10:62–65 (1991), on the other hand, are two methods similar to IPCR which do not require any enzymatic treatment. In RCPCR, two separate PCR reactions, requiring a total of four primers, are needed to generate the mutated product. The separate amplification reactions are primed at different locations on the same template to generate products that when combined, denatured and cross-annealed, form double-stranded DNA with complementary single-strand ends. The complementary ends anneal to form DNA circles suitable for transformation into E. coli.

RPCR is a technique that uses PCR primers having a twelve base exact match at their 5' ends, resulting in a PCR product with homologous double-stranded termini. Transformation of the linear product into recombination-positive (recA-positive) cells produces a circular plasmid through in vivo recombination. Although this method reduces the number of steps and primers used compared to RCPCR, the transformation and recombination of linear molecules is an inefficient process resulting in a correspondingly low mutation frequency.

A modification of site-directed mutagenesis, random mutagenesis, permits the incorporation of random mutations into a polynucleotide. Mutant libraries are normally constructed by the mutagenesis of a small, defined area of a plasmid containing the gene or control region of interest. Methods for generating mutant libraries typically use synthetic oligonucleotides with random or biased mixtures of bases in one or more positions along the oligonucleotide. A variety of methods have been used to introduce these mutagenic oligonucleotides into the expression vector. Typically, the oligonucleotides are hybridized to a substantially complementary strand of DNA and a polymerase is used to extend the length of the oligonucleotide into a polynucleotide whose length is dependant both on the length of the template and on the conditions of enzymatic extension. This procedure permits the construction of large libraries of mutants having mutations in one or more regions of the polynucleotide or protein sequence as compared with the template. From these libraries, the transfectants or transformants can be screened for the desired characteristic. However, both random mutagenesis employing PCR, and random mutagenesis, in general, are restricted in design by the choice of restriction endonucleases traditionally employed for these procedures. Often random mutagenesis has a relatively low efficiency such that a significant number of individual mutations are lost during primer extension and introduction of the polynucleotide into the host. Further, mistakes or unintended mutations are often incorporated into the sequences resulting in an additional decrease in the efficiency. Selected mutations may therefore be under or overrepresented in the library.

Thus, a need exists for a PCR-based mutagenesis method which allows the rapid and efficient alteration of nucleotide sequences to create libraries that are sufficiently diverse. The present invention satisfies this need and provides related advantages as well.

BRIEF DESCRIPTION OF THE DRAWINGS

FIG. 3 is a list of class IIS restriction enzymes and the nucleotide sequence of their recognition sequences (SEQ ID NOS: 5 through 20).

SUMMARY OF THE INVENTION

Figure 1:
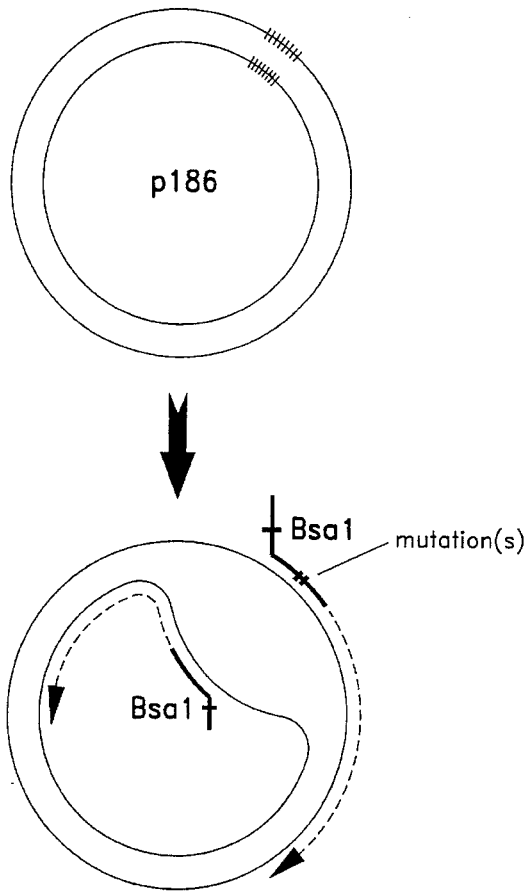
FIG. 1 is a schematic diagram outlining the steps of EIPCR.
Figure 1:
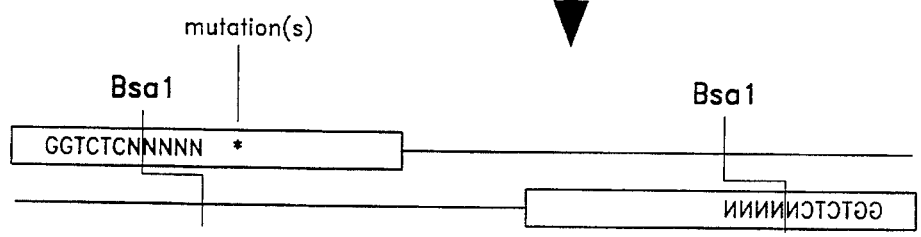
Figure 1:
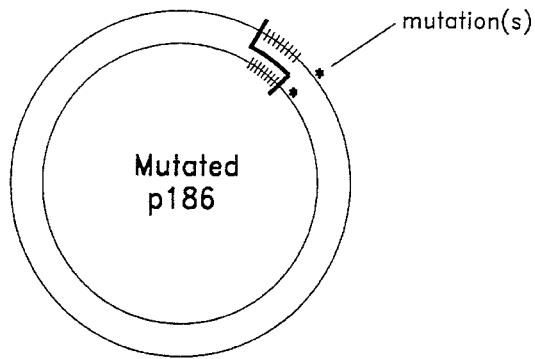

The invention is directed to a method for generating a recombinant mutagenesis library by introducing one or more changes within a predetermined region of double stranded nucleic acid, comprising providing a first primer population and a second primer population, each population having a variable base composition at known positions along the primers, the primers incorporating a class IIS restriction enzyme recognition sequence, being capable of directing change in the nucleic acid sequence and being substantially complementary to the double-stranded nucleic acid to allow hybridization thereto. The method also comprises hybridizing the first and second primer populations to opposite strands of the double-stranded nucleic acid to form a first pair of primer-templates oriented in opposite directions, performing enzymatic inverse polymerase chain reaction to generate at least one linear copy of the double stranded nucleic acid incorporating the change directed by the primer, cutting the double stranded nucleic acid copy with a class IIS restriction enzyme to form a restricted linear nucleic acid molecule containing the change and introducing nucleic generated therefrom into compatible host cells.

In a preferred embodiment, the method additionally comprises the step of joining termini of the restricted linear nucleic acid molecule to produce double stranded circular nucleic acid. The method preferably produces restricted linear nucleic acid molecules containing only the directed change in the nucleic acid sequence. Preferably the double stranded nucleic acid is circular DNA. The method can be performed on either eukaryotic or prokaryotic cells.

In a preferred embodiment of the invention, the double stranded nucleic acid encodes polypeptide. The change in the nucleic acid can be introduced into the amino acid coding region of the polypeptide or into a regulatory region of the polypeptide. Thus changes may be introduced into promoter and enhancer regions of the double stranded nucleic acid. The polypeptide encoded by the double stranded nucleic acid is preferably expressed from the host cells.

In another preferred embodiment of the invention, the double stranded nucleic acid comprises a viral vector and compatible host cells comprise a helper virus packaging cell line that directs the packaging of viral particles containing the viral vector. The viral particles are preferably collected and the method additionally comprises the step of infecting susceptible cells with the viral particles.

In yet another preferred embodiment of the invention, a method is provided for improving polypeptide expression from a double-stranded nucleic acid sequence encoding polypeptide comprising: measuring polypeptide expression from the double stranded nucleic acid in a compatible host cell, providing a first primer population and a second primer population, each of the populations having a variable base composition at known positions along the primers, the primers incorporating a class IIS restriction enzyme recognition sequence, being capable of directing change in the nucleic acid sequence and being substantially complementary to the double stranded nucleic acid to allow hybridization thereto. The method additionally comprises hybridizing the first and second primer population to opposite strands of the double stranded nucleic acid to form a first pair of primer-templates orientated in opposite directions, performing enzymatic inverse polymerase chain reaction to generate at least one linear copy of the double stranded nucleic acid incorporating the change directed by the primers, cutting the double stranded nucleic acid copy with a class IIS restriction enzyme to form a restricted linear nucleic acid molecule containing the change, introducing the nucleic acid from the cutting step or the PCR step into host cells and measuring polypeptide expression from the modified nucleic acid in the cells, and identifying cells with expression levels greater than the expression levels measured in cells containing unmodified double stranded nucleic acid. The method preferably additionally comprises the step of joining termini of the restricted linear nucleic acid molecule to produce modified double stranded circular nucleic acid and the method also preferably comprises the step of obtaining modified template from selected cells. Preferably the modified nucleic acid sequence is identified and transferred into another nucleic acid sequence. The primers can direct changes in a regulatory sequence, including promoters, or the primers can direct changes in a polypeptide sequence. In a preferred embodiment the primers direct changes in a ribosome binding sequence.

In yet another preferred embodiment of this invention, a method is provided for generating a recombinant library using wobble-base mutagenesis comprising: providing a first primer population and a second primer population, said primers being substantially complementary to a region of double stranded nucleic acid encoding polypeptide to allow hybridization thereto, the primers having a variable base composition in the third position of a least one nucleotide codon corresponding to the double stranded nucleic acid and a class IIS restriction enzyme recognition sequence. The method additionally comprises hybridizing the first and second primer populations to opposite strands of the double stranded nucleic acid to form a first pair of primer-templates orientated in opposite directions, performing enzymatic inverse polymerase chain reaction to generate at least one linear copy of the double stranded nucleic acid incorporating the change directed by the primers, cutting the double stranded linear nucleic acid with a class IIS restriction enzyme to form restricted linear nucleic acid molecule containing the change and introducing nucleic acid generated therefrom into compatible host cells. The variable base codons preferably do not alter the corresponding amino acid sequence of the polypeptide.

In a preferred embodiment the primers direct alterations in the leader sequence of the polypeptide. The leader sequence is preferably the bacterial OmpA protein leader sequence or a fragment thereof and the leader sequence is preferably linked to polynucleotide encoding light and heavy chain antibody fragments.

DETAILED DESCRIPTION OF THE INVENTION

The invention provides a novel method for rapid and efficient site directed mutagenesis of double-stranded linear or circular DNA. The method, termed Enzymatic Inverse Polymerase Chain Reaction (EIPCR), greatly improves the utility of previous PCR techniques enabling rapid screening or selection of putative mutant to identify clones containing changes of interest.

In one embodiment, oligonucleotide primers containing the desired sequence changes are used to direct PCR synthesis of a double-stranded circular DNA template (FIG. 1). The primers are designed so that they additionally contain a class IIS restriction enzyme recognition sequence and a sequence complementary to the template for primer hybridization. The primers are hybridized to opposite strands of the circular template and direct the amplification of each strand to form linear molecules containing the desired mutations. The ends of the linear molecules are filled in with Klenow polymerase or T4 DNA polymerase and restricted with the appropriate class IIS restriction enzyme to produce compatible overhangs for circularization and ligation.

EIPCR uses class IIS restriction enzyme recognition sequences in the mutated or non-mutated PCR primers. This type of recognition sequence is used because the cleavage site is separated from the recognition sequence and therefore does not introduce extraneous sequences into the final product. Restriction of the PCR products with a class IIS enzyme removes the recognition sequence and produces homogeneous termini for subsequent ligation. Class IIS recognition sequences therefore circumvent problems associated with ligating heterogeneous PCR termini since such termini will be cleaved off using a class IIS recognition enzyme. If the primers are designed with complementary cleavage sites, the resulting termini will have complementary overhangs which can be used for circularization of the linear molecules. Such complementary overhangs increase the efficiency of intramolecular ligation compared to blunt ends and result in a high percentage of correctly mutated clones. Thus, EIPCR allows efficient mutagenesis and production of homogeneous termini of any DNA template without incorporating extraneous sequences. EIPCR also allows mutagenesis at any location within a circular template independent of convenient restriction sequences.

As used herein, the term "predetermined change" refers to a specific desired change within a known nucleic acid sequence. Such desired changes are commonly referred to in the art as site directed mutagenesis and include, for example, additions, substitutions and deletions of base pairs. A specific example of a base pair change is the conversion of the first A/T bp in the sequence AGCA to a G/C bp to yield the sequence GGCA. It is understood that when referring to a base pair, only one strand of a double-stranded sequence or one nucleotide of a base pair need be used to designate the referenced base pair change since one skilled in the art will know the corresponding complementary sequence or nucleotide.

As used herein, the term "class IIS restriction enzyme recognition sequence" refers to the recognition sequence of class IIS restriction enzymes. Class IIS enzymes cleave double-stranded DNA at precise distances from their recognition sequence. The recognition sequence is generally about four to six nucleotides in length and directs cleavage of the DNA downstream from the recognition sequence. The distance between the recognition sequence and the cleavage site as well as the resulting termini generated in the restricted product vary depending on the particular enzyme used. For example, the cleavage site can be anywhere from one to many nucleotides downstream from the 3' most nucleotide of the recognition sequence and can result in either blunt cuts or 5' and 3' staggered cuts of variable length. Such staggered cuts produce termini having single-stranded overhangs. Therefore, "complementary cleavage sites" as used herein refers to complementary nucleic acid sequences at such single-stranded overhangs. Class IIS restriction enzyme recognition sequences suitable for use in the invention can be, for example, Alw I, Bsa I, Bbs I, Bbu I, Bsm AI, Bsr I, Bsm I, BspM I, Ear I, Esp 3I, Fok I, Hga I, Hph I, Mbo II, Ple I, SfaN I, and Mnl I. It is understood that the recognition sequence of any enzyme that utilizes this separation between the recognition sequence and the cleavage site is included within this definition.

As used herein, the term "substantially complementary" refers to a nucleotide sequence capable of specifically hybridizing to a complementary sequence under conditions known to one skilled in the art. For example, specific hybridization of short complementary sequences will occur rapidly under stringent conditions if there are no mismatches between the two sequences. If mismatches exist, specific hybridization can still occur if a lower stringency is used. Specificity of hybridization is also dependent on sequence length. For example, a longer sequence can have a greater number of mismatches with its complement than a shorter sequence without losing hybridization specificity. Such parameters are well known and one skilled in the art will know, or can determine, what sequences are substantially complementary to allow specific hybridization.

As used herein, the term "a primer capable of directing" when used in reference to nucleic acid sequence changes refers to a primer having a mismatched base pair or base pairs within its sequence compared to the template sequence. Such mismatches correspond to the mutant sequences to be incorporated into the template and can include, for example, additional base pairs, deleted base pairs or substitute base pairs. It is understood that either one or both primers used for the PCR synthesis can have such mismatches so long as together they incorporate the desired mutations into the wild-type sequence.

Thus, the invention provides methods of introducing at least one predetermined change in a nucleic acid sequence of a double-stranded DNA. Such methods include: (a) providing a first primer and a second primer capable of directing said predetermined change in said nucleic acid sequence, said first and second primers comprising a nucleic acid sequence substantially complementary to said double-stranded DNA so as to allow hybridization, a class IIS restriction enzyme recognition sequence and cleavage sites; (b) hybridizing said first and second primers to opposite strands of said double-stranded DNA to form a first pair of primer-templates oriented in opposite directions; (c) extending said first pair of primer-templates to create double-stranded molecules; (d) hybridizing said first and second primers at least once to said double-stranded molecules to form a second pair of primer-templates; (e) extending said second pair of primer-templates to produce double-stranded linear molecules terminating with class IIS restriction enzyme recognition sequences; and (f) restricting said double-stranded linear molecules with a class IIS restriction enzyme to form restricted linear molecules containing said change in said nucleic acid sequence.

Enzymatic Inverse Polymerase Chain Reaction (EIPCR) is a PCR-based method for performing site-directed mutagenesis. Mutations are introduced into a DNA by first hybridizing primers which contain the desired mutations to the DNA, referred to herein as mutant primers. The resulting primer-templates are enzymatically extended with a polymerase to yield an intermediate product. Repriming of the intermediates and polymerase extension will yield the final mutant product. Cohesive termini can be subsequently generated for circularization of the linear products by intramolecular ligation.

The invention is described with particular reference to introducing a predetermined change into a circular template and recircularizing of the product to generate mutant copies of the starting template. However, one skilled in the art can use the teachings and methods described herein to similarly generate mutations in linear templates. The primers designed for use on linear templates are similar to those used for circular templates. Appropriate modifications of primers for use on linear templates are known to one skilled in the art and will be determined by the intended use of the final mutant product. For example, when generating circular products, either from a linear or circular starting template, it is beneficial to use primers containing complementary cleavage sites downstream from the class IIS recognition sequence. Such complementary sites greatly increase the efficiency of intramolecular ligation. With linear molecules, on the other hand, while it is beneficial in some cases for the primers to contain class IIS recognition sequences which produce single-stranded overhangs at their cleavage sites, such cleavage sites need not be complementary. For example, if the product is a linear molecule for subcloning into a vector, cleavage sites which are not complementary can be used for directional cloning of the product. Additionally, a blunt cleavage site can be used to eliminate sequence requirements for subcloning. Thus, depending on the desired product, the cleavage sites within the primers can be complementary or non-complementary.

EIPCR primers are synthesized having three basic sequence components. These sequences are used for generating mutations and for enabling efficient formation of circular products without introducing unwanted sequences or requiring the use of template restriction sequences. The first sequence component, of the primers is the region which directs the predetermined changes. This region contains the desired mutations which are to be introduced into the template. The length and sequence of this region will depend on the number and locations of incorporated mutations. For example, if multiple and adjacent mutations are desired, then the primer will not contain any nucleotides within this region identical to the wild-type sequence. However, if the mutations are not located at adjacent positions, then the nucleotides in between such mutations will be identical to the wild-type sequence and capable of hybridizing to the appropriate complementary strand. Thus, the region can be from one to many nucleotides in length so long as it contains the desired mismatches with the wild-type sequence.

Figure 2:
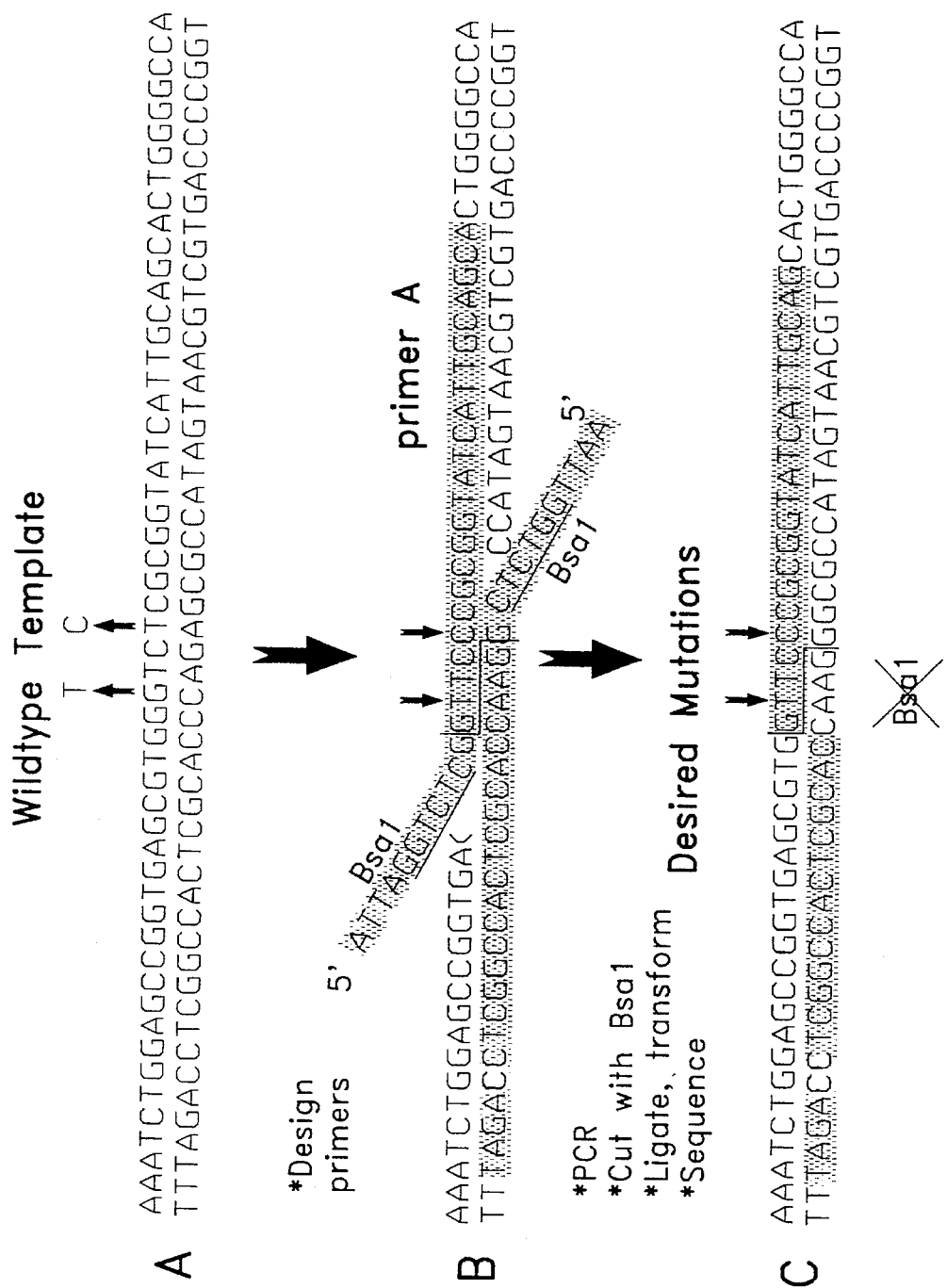
FIG. 2 shows the design of EIPCR primers. Line A shows a region of the PCR template (SEQ ID NO: 1) and two mutations to be made by EIPCR (indicated by small arrows). Line B shows how the primers (SEQ ID NO: 2; SEQ ID NO: 3) relate to the mutated product (line C) (SEQ ID NO: 4). This is not an actual reaction intermediate, but is a cartoon to draw when designing the primers. The primers are indicated in grey. The Bsa I recognition sequence (SEQ ID NO: 5) is underlined. Four or more bases are added 5' to the enzyme recognition sequence of each primer to ensure efficient substrate recognition by the enzyme. Line C shows the sequence of the mutated product. The grey boxes show the parts of the primer that have been incorporated into the final product. The overhangs of the two DNA ends are indicated, but the recognition sequences have been cut off and are not part of the final product.

It is only necessary for one of the primers to contain the desired mutations but a larger number of bases can be mutagenized and a higher efficiency of correct mutations can be obtained if both primers contain the desired mutations on each complementary strand. A strategy for designing EIPCR primers is outlined in FIG. 2. This strategy shows an example of a pair of primers which can be used for mutagenesis at two nonadjacent locations. One skilled in the art can use this strategy and the teachings described herein to design and use primers that incorporate essentially any desired mutation into a double-stranded DNA. The template containing the wild-type sequence is shown in FIG. 2A (SEQ ID NO: 1). Also shown are the desired nucleotide substitutions (arrows). The actual primers are depicted in FIG. 2B as the shaded sequence (SEQ ID NO: 2; SEQ ID NO: 3). The region of each primer containing the desired substitutions is complementary and corresponds to the opposite strand at the same location within the template (FIG. 2C) (SEQ ID NO: 4). For primers A (SEQ ID NO: 2) and B (SEQ ID NO: 3) in FIG. 2B, the mutant region would consist of the sequence GTTCC and its complement, respectively.

The second sequence component of EIPCR primers is the region containing the class IIS restriction enzyme recognition sequence. The location of the recognition sequence is 5' to the mutant region and thus is incorporated at the termini of any extension products. Since recognition sequences are located at the ends of linear extension products, they can also contain additional 5' sequences to facilitate recognition and cleavage by a class IIS enzyme. For example, the primers in FIG. 2B (SEQ ID NO: 2; SEQ ID NO: 3) contain four additional nucleotides 5' to the Bsa I recognition sequence (SEQ ID NO: 5).

Other sequences included within the recognition sequence component of EIPCR primers are the nucleotides between the recognition sequence and the cleavage site. The number of nucleotides will correspond to the distance between these two sites and therefore will vary for different enzymes. For example, the primers of FIG. 2 contain a Bsa I recognition sequence which is cleaved by Bsa I on opposite (SEQ ID NO: 5) strands one and five nucleotides, respectively, 3' to the recognition sequence, leaving a four nucleotide single-strand overhang. Generally, such overhang sequences within the primers are completely complementary to each other but can include limited mutations. Primers are synthesized with filler nucleotides placed 5' to the first cleavage site. The number of filler nucleotides corresponds to the distance between the particular class IIS recognition sequence used and its cleavage site. The sequence of such spacer nucleotides can, for example, correspond to wild-type or non-wild-type sequences or to predetermined mutations. For generating just a few point mutations, it is beneficial to match these nucleotides to the wild-type sequence to increase the hybridization stability of the adjacent mutant primer region.

Types of restriction enzyme recognition sequences to be used in the invention are those recognized by class IIS enzymes. These enzymes recognize the DNA through a sequence specific interaction and cleave it at a discrete distance downstream from the recognition sequence. The ability to cleave such sequences downstream provides a useful means to remove heterogeneous ends and to produce complementary termini for circularization while at the same time removing the recognition sequence from the final product. Specific examples of class IIS recognition sequences have been listed previously and are also listed in FIG. 3 along with their nucleotide sequences and cleavage sites (SEQ ID NOS: 5 through 20). Although recognition sequences having complementary cleavage sites associated with them are preferred, those which have blunt ended cleavage sites can also be used in the invention.

The third sequence component of EIPCR primers is the region to be hybridized to the template DNA. This region must be sufficient in length and sequence to allow specific hybridization to the template. The hybridized portion of the primers must also form a stable primer-template which can be used as a substrate for polymerase extension. It is typically found 3' to the mutant primer region and its sequence is determined with respect to the location of the desired mutations. For example, for the primers shown in FIG. 2 (SEQ ID NO: 2; SEQ ID NO: 3), the hybridization region is twenty nucleotides in length and found 3' to the mutant region. However, the hybridization region can also be 5' to the mutant region. For this orientation, the mutant region must form a stable primer-template which can be used as a substrate for polymerase extension. Longer or shorter hybridization sequences can be used in this region so long as they are appropriately located with respect to the mutant region and also specifically hybridize to the template molecule. One skilled in the art knows or can readily determine the specificity of such hybridization regions for use in EIPCR primers.

Thus, the invention also provides a synthetic primer for introducing at least one predetermined change in a nucleic acid sequence of a double-stranded circular DNA. The primer includes: (a) a class IIS restriction enzyme recognition sequence; (b) said predetermined change in said nucleic acid sequence; and (c) a nucleic acid sequence substantially complementary to said double-stranded DNA. The preferred orientation of the above regions (a) through (c) is in a 5' to 3' direction.

The above described primers can be, for example, hybridized to a double-stranded circular or linear DNA molecule which has first been denatured. Denaturation can be performed, for example, using heat or an alkaline solution. Other methods known to one skilled in the art can also be used.

Hybridization of the primers occurs on opposite strands of the circular template and in a location where the single-stranded overhangs of each primer's complementary cleavage site can be joined together by restriction and ligation. Preferably, such joining should occur so that the wild-type sequence is reformed except for the incorporation of the desired mutations. One way to ensure proper sequence reconstruction is to design the primers such that their complementary cleavage sites overlap and are either identical to the template sequence or contain some or all of the desired mutations. Such primers, once hybridized to a double-stranded circular DNA, form primer-templates and can be extended with a polymerase. The first extension reactions of circular templates result in the synthesis of double-stranded circular products which can be concatenated. Depending on the extent of polymerization, the concatemers can be either partially or completely double-stranded. It is necessary for polymerization to proceed sufficiently far to allow subsequent primer hybridization for a second extension reaction. Smaller circular DNAs result in a greater number of completely double-stranded products and also require shorter extension times compared to much larger circles. Small circular DNAs of less than 1.0 kb are known in the art. Such vectors are beneficial to use in the invention since they can accommodate large inserts (3 to 5 kb) and still be comparable in size to most standard cloning vectors. The plasmid pVX is a specific example of a 902 bp vector, Seed, B., Nuc. Acids Res. 11:2477–2444 (1983), which is incorporated herein by reference. Such vectors can be further modified by the addition of, for example, promoters, terminators and the like to achieve the desired end. Complete extension of a circular DNA of about 5.0 kb can be achieved using the conditions described herein; however, alternative conditions used by those skilled in the art to achieve complete extension of larger circular DNAs can also be used to practice the invention. For linear templates, on the other hand, the first extension reaction produces a double-stranded linear molecule known in the art as the long product.

After one extension reaction, the double-stranded products, whether they exist as circular or linear molecules, have incorporated at one of their ends the EIPCR primer with its associated class IIS restriction enzyme recognition sequence and the desired mutations. These double-stranded molecules can be used for a second cycle of hybridization and extension to produce double-stranded linear molecules which terminate at both ends with EIPCR primers. Further cycles will result in the exponential amplification of template sequence located between each primer on the circular DNA. Thus, the location of the hybridized primers defines the termini of template sequences to be amplified.

Polymerases which can be used for the extension reaction include all of the known DNA polymerases. However, if multiple cycles of hybridization and extension are to be performed, such as required for PCR amplification, then preferably a thermostable polymerase is used. Thermostable polymerases include, for example, Taq polymerase, Vent polymerase and PFU polymerase. Vent and PFU polymerase advantageously exhibit a higher fidelity than Taq due to their 3' to 5' proofreading capability.

Following synthesis of the linear molecules, the products are restricted with the appropriate class IIS restriction enzyme to remove the class IIS recognition sequence and heterogeneous termini and to create cohesive termini used for circularization. The resulting termini correspond to the single-strand overhangs produced after restriction of each primer's complementary cleavage site. To facilitate proper recognition and cleavage, the linear products can be pretreated with a polymerase, such as Klenow, under conditions which create blunt ends. This procedure will fill in any uncompleted product ends produced during amplification and allows efficient restriction of essentially all of the products. After restriction, the cohesive termini can be joined to recirculanze the linear molecule. Covalently closed circles can subsequently be formed in vitro with a ligase. Alternatively, in vivo ligation can be accomplished by introducing the circularized products into a compatible host by transformation or electroporation, for example.

Transformation or electroporation of the circularized products can additionally be used for the propagation and manipulation of mutant products. Such techniques and their uses are known to one skilled in the art and are described, for example, in Sambrook et al., Molecular Cloning: A Laboratory Manual, Cold Spring Harbor, Cold Spring Harbor, N.Y. (1989), or in Ausubel et al., Current Protocols in Molecular Biology, John Wiley and Sons, New York, N.Y. (1989), both of which are incorporated herein by reference. Propagation and manipulation procedures do not have to be performed at the end of all EIPCR reactions. The need will determine whether such procedures are necessary. For example, transformation and DNA preparation can be eliminated if two consecutive EIPCR reactions are to be performed where the product of the first reaction is used as the template for the second reaction. All that is necessary is that the first reaction products are circularized and ligated prior to hybridization with the second reaction primers. Additionally, primers for EIPCR can be used without purification. EIPCR is not as sensitive as other methods to the presence of primers of incomplete length because the non-uniform DNA ends are removed by restriction of the class IIS recognition sequence.

The invention further provides methods of producing at least two changes located at one or more positions within a nucleic acid sequence of a double-stranded circular DNA. The methods include: (a) providing a first population of primers and a second population of primers capable of directing said changes in said nucleic acid sequence, said first and second populations of primers comprising a nucleic acid sequence substantially complementary to said double-stranded DNA so as to allow hybridization, a class IIS restriction enzyme recognition sequence, and cleavage sites; (b) hybridizing said first and second populations of primers to opposite strands of said double-stranded DNA to form a first pair of primer-template populations orientated in opposite directions; (c) extending said first pair of primer-template populations to create a population of double-stranded molecules; (d) hybridizing said first and second populations of primers at least once to said population of double-stranded molecules to form a second pair of primer-template populations; (e) extending said second pair of primer-template populations to produce a population of double-stranded linear molecules terminating with class IIS restriction enzyme recognition sequences; and (f) restricting said population of double-stranded linear molecules with a class IIS restriction enzyme to form a population of restricted linear molecules containing said changes within said nucleic acid sequence. Also provided is a population of synthetic primers for producing at least two changes located at one or more positions within a nucleic acid sequence of a double-stranded circular DNA comprising: (a) a class IIS restriction enzyme recognition sequence; (b) said changes within said nucleic acid sequence; and (c) a nucleic acid sequence substantially complementary to said double-stranded circular DNA.

The method for producing at least two changes located at one or more positions is similar to that described above for site-directed mutagenesis except that the primers can have more than one nucleotide at a desired position. For example, if it is desirable to produce mutations incorporating from two to four different mutant nucleotides at a particular position, then a population of primers should be synthesized such that all mutant nucleotides are represented within the entire population. Each individual primer within the population will contain only a single mutant nucleotide. The proportion of primers containing identical mutant nucleotides will determine the expected frequency of that mutation being correctly incorporated into the final product. For example, if only two mutant nucleotides are desired and each one is equally represented within the primer population, then 50% of the products should contain one of the mutations and 50% should contain the other mutation. If more than two mutations are desired at a particular position or at more than one position, then primer populations should be synthesized which contain individual primers having each of the desired mutations. Primer populations can also be synthesized which direct single mutations at one position and multiple mutations at another position by incorporating one or more mutant nucleotides at the appropriate position.

The design and use of such primers is identical to that previously described for introducing at least one predetermined change into a double-stranded circular DNA. The only difference is that instead of hybridizing a first primer and a second primer to form a pair of primer-templates, hybridization is with a first population of primers and a second population of primers to form a pair of primer-template populations. Each primer-template within the population can include, for example, one of the desired mutant sequences to be incorporated into the resultant products. Amplification of the primer-template population will produce a population of linear products containing all desired mutations. The products can be restricted, circularized and screened for individual mutant clones. Screening can be performed, for example, by sequencing or by expression of polypeptide. Selection can be performed by linking polypeptide expression with the expression of a suitable marker such as an antibiotic resistance gene, luciferase, or the like. Only colonies containing the gene are selected. Following selection, positive colonies can then be screened for a particular characteristic. Expression screening or selection offers the advantage of screening or selecting a large number of clones in a relatively short period of time. These assays permit the identification of clones of interest. Examples of screening and selection assays are well known to those with skill in the art. Each assay is designed and modified for that particular application. Examples of these assays are found in the examples below.

The methods and primers described herein can be used to create essentially any desired change in a nucleic acid sequence. Templates can be linear or circular and result in products containing only the desired changes since class IIS recognition sequences allow the removal of extraneous and unwanted sequences. Product termini which are homogeneous in nature are also produced using the class IIS recognition sequences. Use of circular templates allows the incorporation of mutations at any desired location along the template with subsequent recircularization of the mutant products. Thus, additions, deletions and substitutions of single base pairs, multiple base pairs, gene segments and whole genes can rapidly and efficiently be produced using EIPCR. A specific use of EIPCR would be in the mutagenesis of antibodies or antibody domains. Mutagenesis of antibody complementary determining regions (CDR), for example, can be performed using EIPCR for the rapid generation of antibodies exhibiting altered binding specificities. Likewise, EIPCR can also be used for producing chimeric and/or humanized antibodies having desired immunogenic properties.

The efficiency of incorporating correct mutations into the product using EIPCR can be, for example, greater than about 90%, preferably about 95 to 99%, more preferably about 100%. This efficiency is routinely obtained when using about 0.5 to 2.0 ng of template in a 25 cycle PCR reaction. However, it should be understood that the efficiency directly correlates with the number of amplification cycles and inversely with the amount of template used. For example, the more amplification cycles which are performed, the greater the amount of mutant product present and therefore a larger fraction of mutant sequences will be present within the total sequence population. Conversely, if a large amount of template is used, more amplification cycles are required, compared to using a smaller amount of template, to achieve the same fraction of mutant sequences within the total sequence population. One skilled in the art knows such parameters and can adjust the number of cycles and amount of template required to achieve the required efficiency.

The following examples are intended to illustrate but not limit the invention.

EXAMPLE I

This example shows the use of EIPCR for site-directed mutagenesis of two bases located on a 2.6 kb pUC-based plasmid (designated p186).

The design of the primers and their relationship to the template and to the final mutant sequence is shown in FIG. 2. The 3' end of the primer is an exact match of 20 bases. The 5' ends of the primers comprise the enzyme recognition site and the enzyme cut site, which was designed to form complementary overhangs. Four additional bases were added 5' to the enzyme recognition sequence to facilitate recognition and digestion of the PCR product by the enzyme. Two complementary mutations were designed into each of the primers. Bsa 1 was the enzyme used to make the overhangs (FIG. 3).

PCR reactions were performed in 100 μl volumes containing 0.2–1.0 uM of each unpurified primer, 0.5 ng uncut p186 template plasmid DNA, 1× Vent buffer, 200 uM of each dNTP, 2.5 units Vent polymerase (New England Biolabs, Beverly, Mass.). Thermal cycling was performed on a Perkin-Elmer-Cetus PCR machine (Emeryville, Calif.) with the following parameters: 94° C./3 minutes for 1 cycle; 94° C./1 minute, 50° C./1 minute, 72° C./3–4 minutes for 3 cycles; 94° C./1 minute, 55° C./1 minute, 72° C./3–4 minutes, with autoextension at 4–6 sec/cycle for 25 cycles; followed by one 10 minute cycle at 72° C.

To blunt the ends of the PCR product, the entire reaction mix was supplemented with 8 ul of 10 mM of dNTP mixture (2.5 mM each) and 20 units of Klenow fragment (Gibco-BRL, Gaithersburg, Md.) incubated at 37° C. for 30 minutes. The reaction was then extracted with an equal volume of phenol/chloroform (1:1), ethanol-precipitated, and the pellet was washed and dried. The blunt end product was then restriction digested with Bsa I (New England Biolabs, Beverly, Mass.) as recommended by the manufacturer. The digested DNA was extracted with an equal volume of phenol/chloroform, ethanol-precipitated, as described above, and ligated with 20 units T4 DNA ligase (Gibco-BRL) for one hour at room temperature. Gel-purification of the digested DNA before ligation was not necessary. After ligation, the DNA was transformed into competent DH10B cells recommended by the manufacturer (Gibco-BRL).

Approximately 400 colonies were obtained from a transformation using 10 ng of DNA into 30 ul of frozen competent cells. The transformation efficiency was $4 \times 10^4$ cfu/ug of DNA. Seven colonies were randomly picked and plasmid DNA was prepared for restriction digests. No differences in restriction pattern were seen. The mutated areas of the plasmids of these seven colonies were sequenced. Double-stranded dideoxy sequencing was performed on a Dupont Genesis 2000 automated sequencer using the Dupont Genesis 2000 sequencing kit. The sequences of all seven plasmids contained the desired mutation.

EXAMPLE II

This example shows the use of EIPCR for constructing large libraries of protein mutants.

The binding site of an antibody, called the Fv fragment, normally consists of a heavy chain and a light chain, each about 110 amino acids long. Using molecular modelling tools, several groups have constructed single chain Fv fragments (scFv) in which the c-terminus of one chain is connected by a 10–15 amino acid linker to the n-terminus of the other chain (Huston, Bird, Glockshuber). The single chain construct was shown to be much more stable than the two chain Fv.

Figure 4:
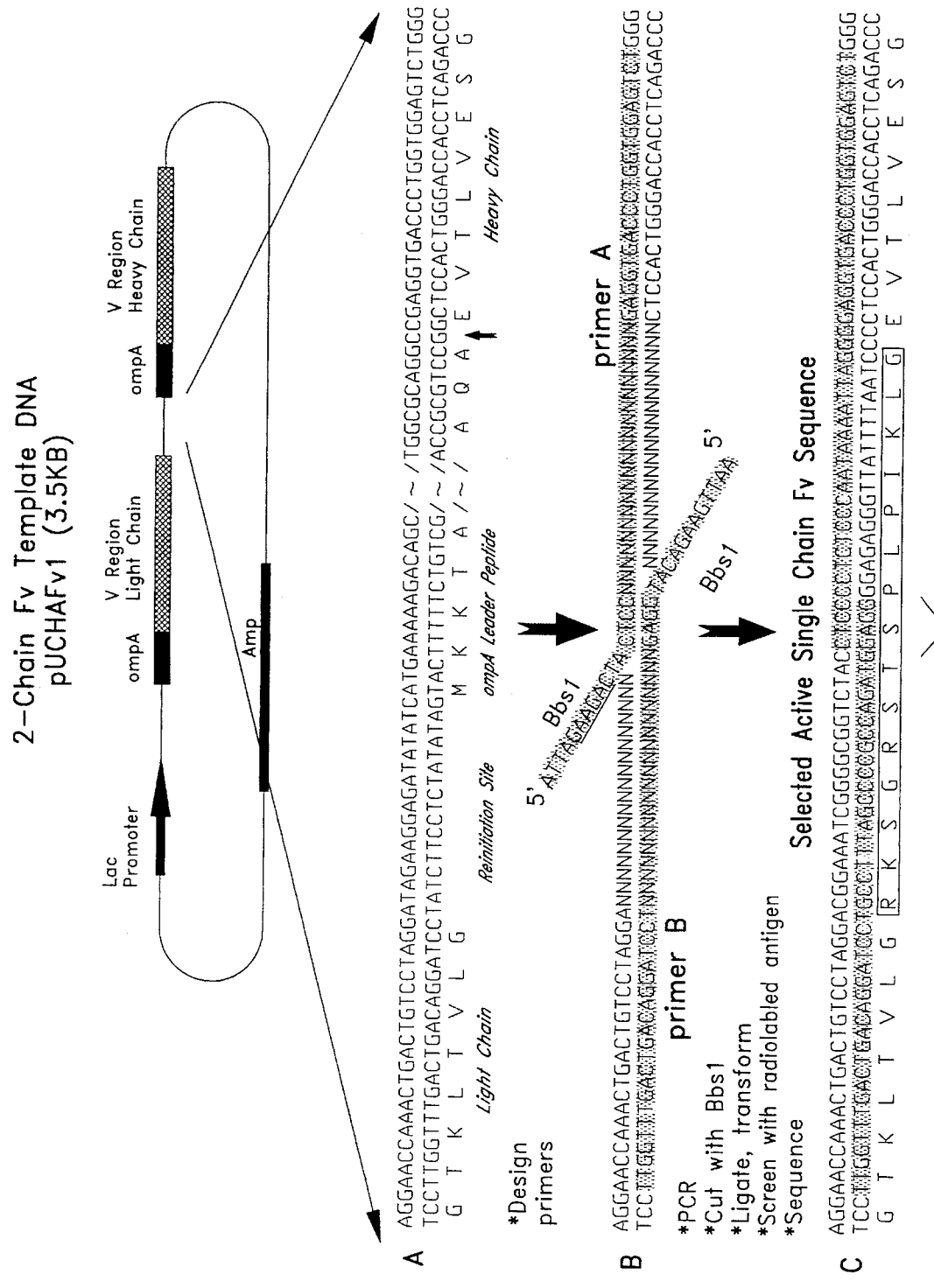
FIG. 4 is a schematic diagram showing the use of EIPCR technology for generating single chain antibodies. Line A shows the template region (SEQ ID NO: 21) to be mutagenized to create a linker between heavy and light chain encoding sequences. Line B shows the EIPCR primer design (SEQ ID NO: 22; SEQ ID NO: 23) and line C shows the nucleotide (SEQ ID NO: 24) and amino acid (SEQ ID NO: 25) sequence of an identified, active single chain antibody sequence.

To eliminate the need for molecular modelling, EIPCR was used to make a large library of different linkers and screen for a scFv clone that is not only active but also expressed at a high level. An antibody was chosen that binds a radioactive Indium chelate, Reardan et al., Nature 316:265–267 (1985), which is incorporated herein by reference. A 3.5 kb pUC-derived plasmid was constructed in which both Fv chains are attached to ompA leader peptides and driven by a Lac promoter (FIG. 4). This plasmid was used as the template for EIPCR in which the DNA between the c-terminus of the first chain and the n-terminus of the mature second chain was replaced by a random mixture of bases, encoding a library of random linkers. The design of the primers is shown in FIG. 4B in the shaded region where N represents an equal proportion of all four nucleotides at the position within the primer population.

Synthesis of the two primer populations used to construct the library was performed on a Milligen/Biosearch 8700 DNA synthesizer. The mixed base positions were synthesized using a 1:1:1:1 mixture of each of the four bases in the U reservoir. The oligonucleotides were made trityl-on and were purified with Nensorb Prep nucleic acid purification columns (NEN-Dupont, Boston, Mass.) as described by the manufacturer.

PCR reactions were performed in 100 μl volumes containing 0.5 uM of each unpurified primer, 0.5 ng pUCHAFv1 template plasmid DNA, 1× Taq buffer, 200 uM of each dNTP, 1 ul Taq polymerase (Perkin-Elmer-Cetus). Thermal cycling was performed on a Perkin-Elmer-Cetus PCR machine with the following parameters: 94° C./3 minutes for 1 cycle; 94° C./1 minute, 50° C./1 minute, 72° C./2 minutes for 3 cycles; 94° C./1 minute, 55° C./1 minute, 72° C./2 minutes, with autoextension at 4 sec/cycle for 25 cycles; followed by one 10 minute cycle at 72° C.

The product of the 100 ul PCR was extracted with an equal volume of phenol/chloroform (1:1), ethanol-precipitated, and the pellet was resuspended in 20 ul KKL buffer (50 mM Tris-HCl pH 7.6, 10 mM MgCl2, 5 Mm DTT; suitable for Klenow, Kinase and Ligase) containing 200 μM dNTPs, 1 mMATP, 10 units DNA Polymerase Klenow fragment and 10 units T4 DNA Kinase and incubated at 37° C. for 30 minutes. Then 10 units T4 DNA ligase were added, and the reaction was continued for 2 hours at room temperature. The enzymes were then inactivated by heating at 65° C. for 10 minutes. The polymerized DNA was then digested with Bbs I (NEB) which cuts off the ends of the PCR fragment, inside the oligos. It was found that Bbs I digestion was inefficient with only four bp 5' to the recognition sequence. To create a longer 5' extension and improve efficiency, the DNA was ligated before digestion. Alternatively, primers could have been synthesized with longer 5' extensions. The digested DNA was then extracted with phenol/chloroform, ethanol precipitated, and resuspended in 20 ul 1× NEB ligation buffer, containing 1 mM ATP and 10 units T4 DNA ligase and the reaction was incubated for 2 hours at room temperature.

One microliter amounts of the ligation reaction were electroporated into 20 ul of DH10B Electromax cells (GibcoBRL, Gaithersburg, Md.) to produce a library of scFv constructs. The Gibco-BRL electroporator and voltage booster was used as recommended by the manufacturer. Cells were plated at 3,000 cfu/plate on plates containing 0.05 mM IPTG, to induce Fv expression.

For screening, the labelled chelate was prepared by incubating 10 ul of 0.075 mM Eotube chelate with 50 uCi of buffered [111]Indium Chloride in a metal free tube. Colony lifts of the petri plates containing the protein library were prepared using BA83 nitrocellulose filters (Schleicher and Schuell, Keene, N.H.). The filters were blocked by incubation in Blotto (7% non-fat milk in PBS) for 10 minutes, washed with PBS, followed by incubation in Blotto containing 10 uCi of [111]Indium Chloride per filter for 1 hour at room temperature. The filters were then washed repeatedly with PBS for a total of 15 minutes, dried and exposed to Kodak X-omat AR autoradiography film for several hours.

The quality of the protein library was determined by DNA sequencing of the linker of several unscreened clones. Sequencing was performed as described in Example I. The composition of the mixed site residues was 19% G, 31% A, 25% T, 25% C (n=119).

The size of the library was determined by plating. In a typical electroporation, 30,000 cfu's were obtained from electroporation of 1 ul of ligation mixture into 20 ul of cells. The ligation contained 0.1 ug of DNA in 20 ul. The library size was about $3\times10^5$ recombinants and the electroporation efficiency was $6\times10^6$ cfu/ug. Approximately 30,000 clones were screened, and about 60 colonies gave a range of signals on the primary screen (0.2%). Those with the strongest signal were colony purified and the DNA sequence of the linker was determined. The sequences of one linker from an identified scFv clone is shown in FIG. 4C.

LIBRARY MUTAGENESIS

Library mutagenesis using a heterogenous primer population permits incorporation of a large number of mutations into a population of host cells to generate a recombinant library. The resulting mutations are typically introduced into a polynucleotide suitable for cell delivery. The polynucleotide can additionally be adapted for expression. These polynucleotides may contain changes in either the regulatory region of the polynucleotide or in a translatable region. The directed mutations in the polynucleotide sequence may alter levels of protein expression, alter a functional characteristic of a protein, or confer a particular cell phenotype. The incorporation of a large number of mutations into a host population is termed library mutagenesis. In general, libraries can be prepared and screened for changes in any measurable cell property. Similarly, the transformed or transfected cells containing the altered nucleic acid sequences can be screened or selected for a desired polynucleotide sequence independent of polypeptide expression.

There are several different methods for performing library mutagenesis that are available to those of skill in the art. A number of these methods use PCR to produce a library of mutant constructs. However, none of the existing methods for making mutant libraries are based on inverse PCR.

Enzymatic Inverse PCR (EIPCR) amplifies the entire plasmid, a portion of the plasmid or linear sequence of a polynucleotide. These methods differ from other mutagenesis methods in the use of class IIS restriction sequences in the 5' end of both primers. Digestion with class IIS restriction enzymes, such as BsaI (GGTCTCN'NNNN), which have their recognition sequence 5' to, and separated from, their cleavage site allows the removal of the entire recognition sequence prior to ligation. This preferably leaves the linear PCR product with compatible overhangs at each end. Intra-molecular ligation of the PCR product yields a full-length circular plasmid.

An important advantage of EIPCR library mutagenesis is that any plasmid or DNA fragment can be used to create a library of mutations. The only limitation is the efficiency of the PCR process. The generation of a complementary strand is limited by the length of the template and by the elongation rate of the polymerase. It is likely that advances in the PCR technology, in particular, enzyme efficiency, will permit long DNA fragments to be used in this invention. The library mutagenesis methods disclosed herein are rapid and efficient and permit one of skill in the art to generate several libraries in a day. For example, once primers are prepared, libraries such as those prepared in Example III can be generated in 6 to 10 hours.

In EIPCR library mutagenesis, the entire plasmid is amplified using mutagenic primers. The simple design of EIPCR results in a high efficiency of ligation of mutant plasmids, thus generating a high level of diversity in the library. The higher the level of genetic diversity in a recombinant library, the more likely the library will contain a mutant of interest readily identifiable by methods known to one of skill in the art. Another important benefit of EIPCR over other methods for library mutagenesis is that, as in EIPCR site-directed mutagenesis, mutations can be made in any area of the sequence independent of available restriction sequences. Restriction endonuclease recognition sites are not incorporated into the final construct. The usefulness of EIPCR for library mutagenesis, is described in Example III and illustrated in FIG. 5.

A method for performing library mutagenesis to generate a recombinant library by introducing changes within a predetermined region of linear or, preferably, circular double stranded DNA is contemplated herein. The method comprises (a) providing a first primer population and a second primer population, each having at least one variable base at known complementary positions along the primers capable of directing a change in the nucleic acid sequence, the first and second primer populations being substantially complementary to the double-stranded nucleic acid to allow hybridization thereto and having a class IIS restriction enzyme recognition sequence and cleavage sites, (b) hybridizing the first and second primer populations to opposite strands of the double stranded nucleic acid to form a first pair of primer-templates oriented in opposite directions, (c) performing enzymatic PCR as herein before described, (d) cutting the double stranded linear molecules with a class IIS restriction enzyme to form restricted linear polynucleotide sequences containing the change in said nucleic acid sequence, thereby removing restriction endonuclease recognition sites, (e) optionally joining termini of the restricted linear molecules of step (d) to produce a double-stranded circular polynucleotide sequence, and (f) introducing polynucleotide sequence obtained from step (d) or (e) into compatible host cells.

The term "primer population" is used to describe the pool of primers that have identical base compositions except at certain predetermined locations along the sequence that contain a variable composition. The primers for EIPCR library mutagenesis are otherwise designed similar to those primers used for EIPCR site-directed mutagenesis. Primer pairs for EIPCR mutagenesis are designed to hybridize to the top and bottom strands of a double stranded template and to extend in opposite directions. The primers are chosen to be substantially complementary to that region of the nucleic acid template to be mutagenized. These primers may be overlapping on the template, contiguous, or non-overlapping.

The primer pairs are substantially complementary to the template to facilitate hybridization during the PCR process. Preferably, the primer contains at least a 15 base region at the 3' end of the primer that is complementary to the template. Other regions of complementarity may be interspersed throughout the length of the primer. The primer additionally contains a class IIS restriction endonuclease recognition sequence and a region containing noncomplementary bases that confers the desired variable mutation. The variable region can be of any length, the only restriction on length being the ability of the primers to hybridize to the template and direct synthesis of a substantially complementary strand of DNA. Further, the variable region or regions may be interspersed between complementary regions along the primer strand. Filler base regions can additionally be added to the primer at the 5' end of the primer, before the class IIS recognition sequence, and between the class IIS recognition sequence and the class IIS cleavage site. Any final primer length is contemplated within the scope of the invention. Primer length is limited only by the efficiency of the oligonucleotide synthesizer. Primers may be prepared by methods known to those of skill in the art. Those with skill in the art will be readily able to determine if a given primer adequately hybridizes to a given template and is thus suitable for amplification using EIPCR.

The extent of primer variability desirable for library mutagenesis is determined during primer synthesis. A mixture of nucleotides, or polynucleotides such as amino acid encoding trimers, are introduced at one or more positions along the primer oligonucleotide. The addition of trinucleotide fragments during synthesis provides direct control over amino acid mixtures. The nucleotide mixture is formulated to contain a predetermined percentage of each of the four bases. These percentages may vary from 0% to less than 100% for any one base and from 0 to 100% for each of the 64 amino acid encoding trimers. The frequency of a given sequence is determined by the desired probability that a particular base or trimer will be present at a particular position along the primer. Thus, for example, if the library is to contain variable mutations at position 6 of the primer oligonucleotide corresponding to a 75% average likelihood that position 6 is guanosine and a 25% average likelihood that position 6 will be adenosine, then the elongating primer will be exposed to a mixture of ¾ guanosine and ¼ adenosine at position 6. These mixtures can also be prepared in proportions such that for a region of 10 bases it is likely that on average only one of the 10 bases in any primer is different from the template sequence. This provides a primer pool that theoretically represents every possible permutation in each nucleotide position over a 10 base pair sequence. A review of primer preparation and design in random mutagenesis can be found in *Oligonucleotides and Analogues: A Practical Approach* (F. Eckstein Ed., Oxford University Press, 1991) and Hermes et al., Gene 84:143–151, 1989, which is hereby incorporated by reference.

Figure 6:
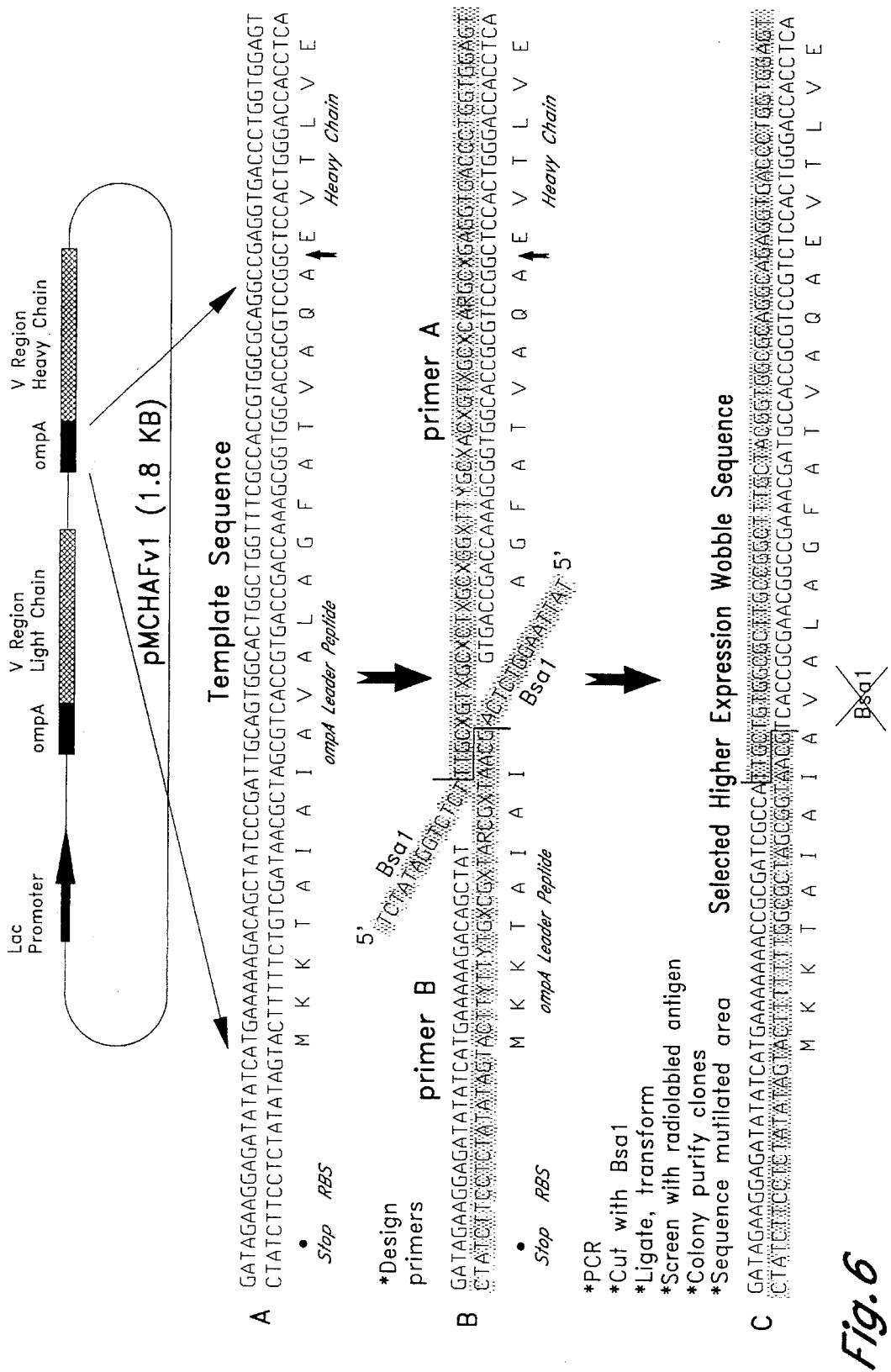
FIG. 6 is a schematic of EIPCR primer design. Line A shows the area of the wildtype leader sequence that was replaced by a library of leader sequences. Line B shows the design of the mutagenic primers relative to the template (SEQ ID NO: 26 and SEQ ID NO: 27). Line C shows the sequence of the identified, positive single chain Fv linker conferring increased protein expression that was obtained from the random library (SEQ ID NO: 28).

As illustrated in FIG. 6 the primer pairs contain a complementary region at the class IIS restriction endonuclease cleavage site. In EIPCR library mutagenesis, this overlapping region preferably does not contain a mutation. This ensures that recircularization of the template can occur following PCR amplification. In the examples that follow, class IIS restriction endonuclease BsaI is used to generate a four base overhang at each end of the nucleotide sequence. FIG. 3 provides an exemplary list of other class IIS restriction endonucleases, contemplated within the scope of this invention.

Library mutagenesis can be used to alter any region within a nucleic acid sequence. These mutagenesis procedures are particularly useful for generating a library of mutations within the mature region of a protein sequence, within a leader sequence, or within sequences that do not encode protein. Sequences that do not encode protein may influence or regulate protein expression. These include, but are not limited to non-coding regions on the DNA, for example, enhancer sequences, promoter regions, sites for DNA binding proteins such as repressors, Z-DNA formation, matrix associated regions, telomeres, origins of replication and recombination signals. In addition to those non-coding regions on the DNA that are transcribed, non-coding regions on mRNA additionally contemplated include, but are not limited to snRNP's, spliceosomes, ribosome binding sites, regions of secondary structure, terminators, stability sites and cap sites. It is additionally contemplated within the scope of this invention that EIPCR library mutagenesis can be used to generate recombinant libraries containing altered sequences corresponding to tRNA or rRNA. Mutations in regulatory regions of a nucleic acid sequence can effect the level of protein expression, while in-frame substitution mutations within the nucleic acid sequence encoding protein can effect protein function. It is therefore contemplated that the procedures described herein will be useful for generating recombinant libraries having mutations in any of these aforementioned regions of the nucleic acid.

EIPCR library mutagenesis can be used to alter the functional characteristics of a particular protein. A protein sequence engineered into an expression construct can be used as a nucleic acid template for EIPCR library mutagenesis. Like other forms of library mutagenesis, this procedure can be used, for example, to mutagenize a binding region on a polypeptide, thereby generating an expression library that can be screened or selected for altered binding characteristics. EIPCR mutagenesis can also be employed to mutate a region of a polypeptide sequence that influences intramolecular binding. For example, a polypeptide region that links two protein domains involved in ligand binding can be mutated, using the methods disclosed herein, to optimize the interactions between the protein domains.

One type of mutagenesis contemplated within the scope of this invention is wobble base library mutagenesis using EIPCR. Wobble base mutagenesis incorporates mutations within the primer population in positions that correspond to the third position of a nucleotide codon. Most mutations in the third position of a codon do not alter the amino acid sequence of the resulting polypeptide. Accurate tRNA-mRNA pairing is required at the first two positions within the codon during translation. The third position can tolerate pairing with more than one tRNA and this degeneracy is termed a "wobble". Thus the same amino acid sequence can be derived from several different nucleotide sequences.

Alterations in the nucleotide sequence that do not affect the protein sequence may alter the level of protein synthesis or expression within a given host. In particular, alterations in the nucleic acid sequence of the leader portion of a polypeptide can influence levels of protein synthesis from one protein to another or from one host to another. An example of two primers designed to confer alterations in the OmpA leader sequence that result in increased levels of antibody Fv fragment expression from *E. coli* is found in FIG. 6. Once a leader sequence is optimized for the expression of one particular polypeptide, using EIPCR library mutagenesis, within a given host, it is further contemplated that this leader sequence can then be linked to other gene sequences encoding polypeptide to optimize expression of other polypeptide. Similarly it is also contemplated within the scope of this invention that other regulatory regions can be optimized using EIPCR library mutagenesis and that these optimized regions can be engineered into other expression constructs for maximal expression of other polypeptides in vitro or in vivo.

The invention is preferably designed to incorporate one or more random changes within predetermined regions of a circular template, such as a vector. Vector choice is determined first by the choice of host cell used to create the desired library. It is well known to those of skill in the art that vectors are commercially available for protein expression in prokaryotic and eukaryotic systems. Expression vectors are available for bacteria, yeast and mammalian systems. In addition, viral vectors for both eukaryotic and prokaryotic cells are also contemplated within the scope of this invention. Expression vectors are required when the translation products from the mutated nucleic acid sequences are to be assayed. An analysis of random mutations in nucleic acid may not require the use of an expression vector where mutations can be screened using polynucleotide probes or the like. Those with skill in the art will be able to choose an appropriate commercially available vector, create their own vector, or recreate the exemplary vector described in Example V below.

It is additionally contemplated within the scope of this invention that EIPCR library mutagenesis could be performed on one region of nucleic acid within a construct, and a second (and/or subsequent) mutagenesis procedure be performed on another region of a construct or on a separate nucleic acid construct. Following amplification, these sequences can then be combined to produce a construct with two or more regions of random mutagenesis.

A general description of the hybridization of aliquots of the first and second primer pools to the nucleic acid template as well as a general description of EIPCR are disclosed in the detailed description of site-directed mutagenesis beginning on page 16. The term "inverse" in enzymatic inverse polymerase chain reaction is used to describe the primer pair orientation during the PCR process such that at the initiation of elongation the 3' end of the primers are directed away from one another. The mechanics of hybridization and nucleic acid sequence amplification in library mutagenesis are similar to, if not identical to, those employed in EIPCR site-directed mutagenesis and will not be repeated here. Thus, the term "performing EIPCR" as a step in the production of a library of mutations following the hybridizing step of the primers to the template, comprises 1) extending the first pair of primer-templates to create double stranded molecules; 2) denaturing the primer templates; 3) hybridizing the first and second primers at least once to the double stranded molecules to form a second pair of primer-templates; 4) extending the second pair of primer-templates following hybridization to produce double-stranded linear molecules terminating with class IIS restriction enzyme recognition sequences; and 5) repeating steps 1–3 as needed.

Once mutated linear template has been generated in sufficient quantity, the appropriate class IIS restriction enzyme is used to cleave the nucleic acid to create termini compatible for ligation. Ligation of the linear molecules is performed under conditions that favor recircularization of the plasmid. These conditions are well known to those with skill in the art and exemplary conditions are described in Example III.

The nucleic acid is next introduced into the desired host cells. The nucleic acid can be introduced into the host cells by any means known to those of skill in the art. These methods include, but are not limited to methods to prepare competent bacterial cells including $CaCl_2$ treatment, and methods to transfect eukaryotic cells including $CaPO_4$ precipitation, liposome mediated transfection, viral infection, or electroporation. The method for introducing nucleic acid into the host cell will, in part, be determined by the host cell type. Descriptions of each the transformation and transfection procedures are found in recombinant methodology handbooks including those of Sambrook et al. or Ausubel et al. (supra.) Following transfection, transformation or infection, the cells are expanded and screened for the desired cell function. There are a variety of screening assays that are available to the investigator. Assay design should reflect the desired goal of mutagenesis. For example, the assay disclosed in Example III below is designed to detect increased levels of expression of a particular antibody fragment in *E. coli*. Assays can also be designed to detect increases in the binding constants ($K_a$) of an antibody or receptor to its antigen or ligand. Other assays can be designed to detect changes in the level of protein expression or changes in the functional activity of a protein. For example, in a eukaryotic system, the increased ability of a protein to promote growth or stimulate a particular cellular function can be measured by removing cell supernatants from mutated cells or their progeny, adding this supernatant to susceptible cells, and assaying for growth promoting activity. Those with skill in the art will be able to select an appropriate screening or selection assay for a particular library to identify a particular clone of interest.

In a second example, EIPCR library mutagenesis can be used to alter the expression of one polypeptide in relation to a second polypeptide. Thus in Example III below, random mutagenesis is used to increase the level of Fv heavy chain expression, thereby equalizing levels of heavy and light chain Fv fragment expression.

In general once a particular mutation is identified as conferring a desired property to a protein sequence, the cells are selected and expanded. The nucleic acid containing the desired mutation is isolated and sequenced. Identified sequences from mutations in regulatory regions of a nucleic acid sequence can then be genetically transposed to other expression systems. Thus, a contemplated method within the scope of this invention is one that identifies an optimized nucleic acid sequence derived from EIPCR library mutagenesis to promote an increase in the level of protein expression as compared with wildtype sequence.

The following examples of random EIPCR library mutagenesis are provided below. These examples are intended to illustrate but not limit the invention.

EXAMPLE III

This example illustrates a preferred embodiment of EIPCR library mutagenesis, wobble base mutagenesis. In wobble base mutagenesis, mutations are introduced into the nucleic acid sequence without altering the amino acid sequence of the target protein. In this example, the leader or signal sequence of a protein is variably mutated in the third base position of at least one codon to generate a recombinant library that can be screened for colonies with increased levels of eukaryotic protein expression as compared with non-mutated controls. The expression level of foreign proteins in E. coli is determined by a large number of factors, and expression level optimization is normally a slow and tedious process. For secreted proteins, like the exemplary antibody Fv fragments used here, optimization of expression is complicated by the difficulties associated with secreting a eukaryotic protein in a prokaryotic system. Without the optimized modifications generated by EIPCR library mutagenesis, described below, secretion and expression of eukaryotic proteins in prokaryotic systems is very low.

In this particular example, expression of Fv fragment expression of an anti-metal-chelate antibody (CHA255) was optimized in E. coli. The Fv fragment was expressed in active form in the periplasm of E. coli. Both the heavy and light chains of the Fv fragment, each with its own leader peptide, were placed under the control of a Lac promoter on a 1.8 kb plasmid, The CHA255 antibody binds a chelated radioactive metal ($^{111}$Indium or $^{90}$Y chelate complex) to provide a simple screening assay to permit detection of functional antibody fragments. For optimization of expression or mutagenesis of other proteins and antibodies, other screening systems may be useful.

Expression Vectors

Figure 5:
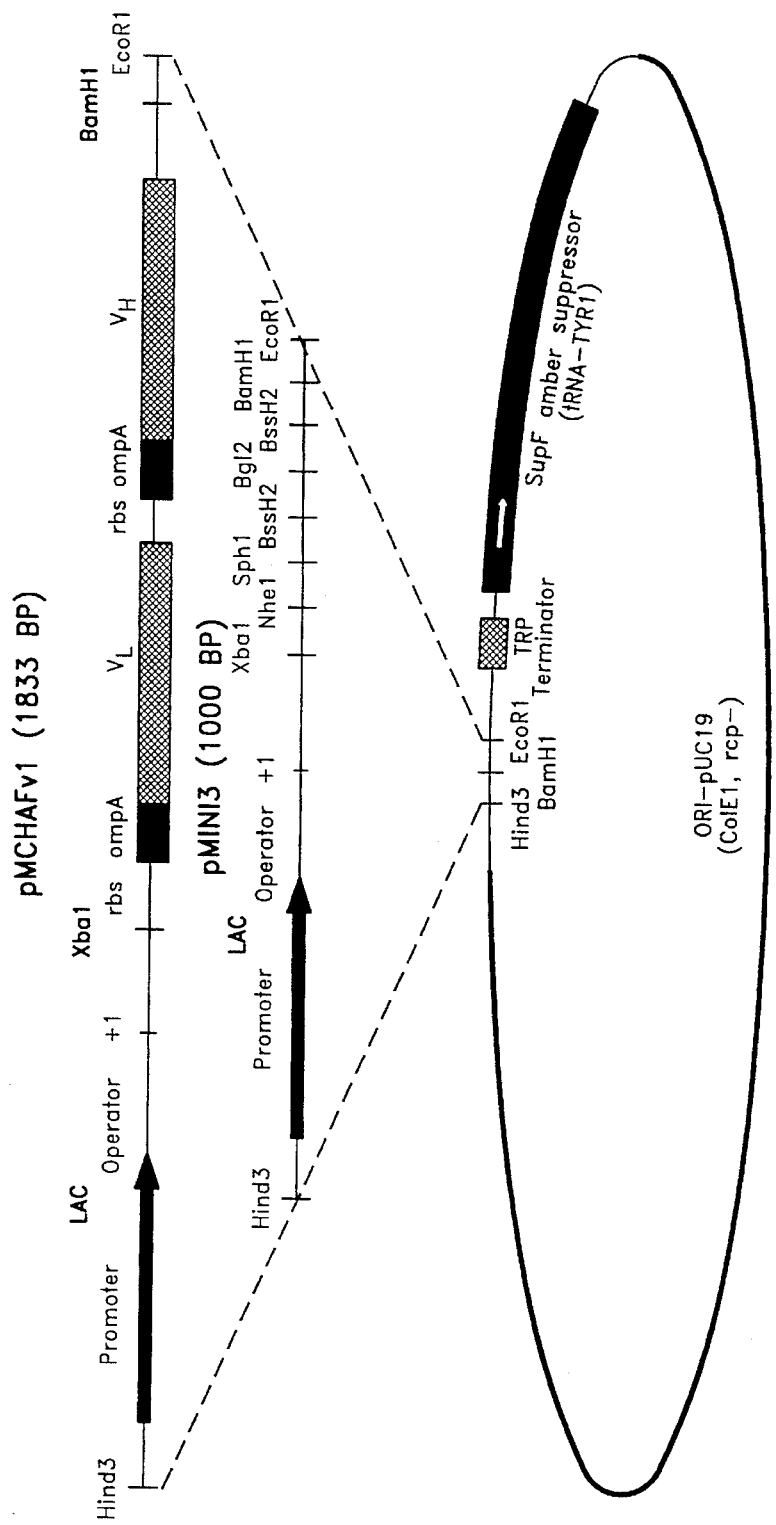
FIG. 5 is a schematic of the 1.8 kb expression vector pMCHAFv1 for CHA255 Fv fragment expression. The expression cassette is located between Hind III and Eco R1 restriction endonuclease sequences in pUC19.

Any expression vector that can be amplified together with its insert is contemplated within the scope of this invention. However, we have chosen to exemplify a relatively small plasmid (<7kb) that is readily amplified by PCR. pMCHAFv1, the 1.8 kb expression vector used for EIPCR mutagenesis and Fv expression, is shown in FIG. 5. The nucleic acid sequence encoding light chain of the Fv fragment is 5' to the nucleic acid sequence encoding the heavy chain of the Fv fragment. Each chain has its own OmpA signal peptide, and both chains are driven by a single Lac promoter. The OmpA signal sequence and Lac promoter sequence are provided in references from Movva et al. and Reznikoff et al. respectively, which are hereby incorporated by reference (Movva et al., J. Biol. Chem 255:27–29, 1980, J. Mol. Biol. 143:317–328 (1980) and Reznikoff et al. (1980) "The Lac Promoter". *The Operon*. Miller et al. Eds. Cold Spring Harbor Press, N.Y.) The antibody genes for CHA255 are the same as those used in Example I above. The codons of the light and heavy chain are those obtained from the original mouse antibody sequence. Similarly, the OmpA leader sequence is the native sequence obtained from the OmpA protein nucleic acid sequence as described in Example I. pMCHAFv1 was constructed from pMINI3 (FIG. 5). pMINI3 is a 1.0 kb expression vector which contains a synthetic Lac promoter, supF (derived from tRNA-tyr, Huang et al., supra.) as the selectable marker, and a rop ColE1 origin, obtained from pUC (Pharmacia, Piscataway, N.J.). The supF vectors are designed to be used with commercially available chemically or electro-competent E. coli MC1061/P3 cells (Invitrogen Inc., San Diego, Calif.). These cells contain amber mutations in both the ampicillin and tetracycline drug resistance genes, located on a P3 incompatibility group plasmid. Thus the P3 plasmid can co-exist with ColE1 incompatibility group plasmids such as pUC. The P3 plasmid is too large to interfere with pUC plasmid purification. Transformants are selected on plates with 25 ug/ml ampicillin and 7.5 ug/ml tetracycline.

Oligonucleotide Synthesis for Wobble Mutagenesis

The two oligonucleotides used to construct the library are shown schematically in FIG. 6B. The oligonucleotides are designed to hybridize to opposite DNA strands of the pMCHAFv1 template adjacent to the OmpA leader sequence. The resulting DNA and mRNA derived from this pool of mutated oligonucleotides is a library of sequences, all encoding the same OmpA protein sequence. The X in FIG. 6B corresponds to the variable positions within the primer population. The sequences are provided as SEQ ID NO: 26 and SEQ ID NO: 27. Here the N corresponds to the X in FIG. 6B. Primer oligonucleotides also contain R and Y base designations. The R indicates the incorporation of a purine and the Y indicates the incorporation of a pyrimidine. The limitation of purines or pyrimidines in the third position of the codon ensures that the amino acid sequence is not modified by the incorporation of random nucleotides. Constant regions within the primer are coded by the appropriate base designation. The primers (moving 5' to 3)' contain, as indicated, filler sequence, a BsaI class IIS restriction endonuclease recognition site, filler sequence, a BsaI cleavage site that forms the cohesive termini for circularization, a region comprising random base positions in the third position of the nucleotide codon, and a complementary region to anchor the primer to the template during hybridization. Oligonucleotide synthesis was performed on a Milligen/Biosearch 8700 DNA synthesizer (Milligen, Burlington, Mass.). The mixed base positions were synthesized using a fresh 1:1:1:1 molar mixture of each of the four bases in the U reservoir. The oligonucleotides were made trityl-on and were purified with Nensorb Prep nucleic acid purification columns (NEN-Dupont, Boston, Mass.) as described by the manufacturer.

Amplification Conditions and Generation of Modified Template

PCR was performed in a 100 µl volume. Each reaction contained 0.5 µM of each purified primer, 0.5 ng pMCHAFv1 template plasmid DNA, 1× Taq buffer, 200 µM of each dNTP and 1 µl Taq polymerase (Perkin-Elmer-Cetus) The thermo-cycling parameters were: 94° C./3 min for 1 cycle; 94° C./1 min, 50° C./1 min, 72° C./2 min for 3 cycles; 94° C./1 min, 55° C./1 min, 72° C./2 min, with autoextension at 5 sec/cycle for 10 cycles; 94° C./1 min, 55° C./1 min, 72° C./3 min, 1 with autoextension at 8 sec/cycle for 12 cycles; followed by one 10 min cycle at 72° C. In a PCR reaction, the primers direct the amplification of a linear DNA sequence of equal length to the template plasmid with an additional 11–14 bp extensions at each end of the DNA that includes the class IIS restriction sequence.

PCR Product Manipulations

The DNA obtained from 2–4 100 μl PCR reactions was flushed by addition of dNTPs to 200 μM, 50 units DNA Polymerase Klenow fragment and 30 units T4 DNA Kinase and incubated at 37° C. for 30 minutes. After phenol/chloroform extraction and precipitation, the DNA was digested with BsaI (New England Biolabs, Beverly, Mass.). The digested DNA was gel purified, ethanol precipitated, and ligated at low concentration and without polyethylene glycol to favor intramolecularinteractions, thus favoring circularization of the nucleic acid as opposed to concatamer formation. The ligation was ethanol precipitated using ammonium acetate, washed twice with 80% ethanol, vacuum dried and resuspended in 20 ul 0.1× TE (Sambrook et al., supra.) for electroporation. After digesting the 12–14 bp overhang with BsaI, the resulting cohesive termini were ligated intramolecularly, and the ligation was electroporated into E. coli for expression analysis.

Electroporation

One microliter amounts of the ligation reaction were electroporated into 20 ul of MC1061/P3 cells (Invitrogen, San Diego, Calif.) using the Invitrogen electroporator. Cells were plated on 23×23 cm plates as described above.

Cell Growth Conditions

For routine cell growth that does not require foreign protein expression, the cells were grown in M9CA media (Merril et al., Proc. Natl. Acad. Sci. (U.S.A.) 74:4335–4339, 1979) which is hereby incorporated by reference.

For colony lift screening assays, the cells were plated on 23×23 cm plates with CS agar (48 g/l yeast extract, 24 g/l tryptone, 3 g/l NaH2PO4, 3 g/l Na2HPO4, 15 g/l agar) with 0.5 ug/ml isopropylthiogalactoside (IPTG) (Boehringer Mannheim, Indianapolis, Ind.) for induction of protein expression.

For expression level determination, clones were grown in CS broth with 0.2 mMIPTG in baffled shaker flasks at 250 rpm for 30 hours at 30° C., with a boost of 0.2 volumes of 240 g/l yeast extract and 120 g/l tryptone after 18 hours. The Fv expressing constructs were grown at 30° C. CS broth permits the use of higher levels of IPTG before overexpression of the foreign protein causes bacterial death. Thus, with CS broth most of the Fv protein can be found in the media rather than in the bacterial periplasm.

Size Determination of the Random Library

The molar ratios of fresh bases were reflected accurately in the oligonucleotide pool as determined by the methods of Hermes et al. (Proc. Natl. Acad. Sci. (U.S.A.) 87:696–700, 1990) which is hereby incorporated by reference. The ratio of bases in the mixed sites within the PCR product was verified by DNA sequencing a representative sampling of individual clones. The composition of the mixed site residues in the PCR product was 19% G, 31% A, 25% T, 25% C (n=119).

The theoretical maximum complexity of the library is $8 \times 10^9$ different sequences. The actual size of the library was determined by plating. In a typical electroporation, $5 \times 10^5$ colony forming units (cfu) were obtained from electroporation of 1 μl of ligation mixture into 20 μl of cells. The ligation contained 0.5 μg of DNA in 20 μl. The library size is thus about $1 \times 10^7$ and the efficiency was $2 \times 10^7$ cfu/ug. For this particular example, the screening assay was found to be more limiting than library size.

Colony Screening Assay

Colony lifts of 23cm×23cm plates with $0.3-1 \times 10^5$ colonies were prepared using BA83 nitrocellulose filters (Schleicher and Schuell, Keene, N.H.). The filters were blocked by incubation in 3% non-fat milk in 25 mM Tris-HCl pH7.5 for 10 minutes, washed with 25 mM Tris, followed by incubation in 25 mM Tris containing 50 uCi of chelated $^{111}$Indium or $^{90}$Yttrium per filter for 1 hour at room temperature. The filters were then washed with 25 mM Tris for a total of 15 minutes, dried and exposed to Kodak X-omat AR autoradiography film for several hours.

Approximately $5 \times 10^5$ clones were screened, and a wide range of signals were obtained on the primary screen. Bacterial colonies that corresponded to strong filter signals were purified by replating. These were again assayed for activity. Two colonies with very strong signals were colony purified and reassayed. The expression level of these two clones was about ten times that of the wildtype. Assay design for the expression of other antibody fragments in E. coli is outlined by Skerra et al. (Anal. Biochem. 196:151–155, 1991) which is hereby incorporated by reference.

Elimination of the Effect of Unintended Mutations

With any mutagenesis procedure there is a risk of introducing mutations in areas other than the target. To demonstrate that the observed increase in protein expression was the result of the nucleic acid sequence identified from the selected clone, a 130 bp fragment containing the mutated area was cloned back into wildtype pMCHAFv1 DNA. This construct expressed more protein than the wildtype sequence, proving that the 10-fold increase in the level of protein expression as compared with wildtype controls is the result of the mutated sequence.

DNA Sequencing

The sequence of the 130 bp fragment, containing the mutation that conferred increased protein expression was determined by double stranded dideoxy sequencing on a Dupont Genesis 2000 automated sequencer using the Dupont Genesis 2000 sequencing kit. The DNA sequence of the 130 bp fragment differed from the wildtype sequence only at the targeted wobble bases, confirming that the amino acid sequence was not altered by the mutagenesis procedure. No mutations outside of the targeted wobble bases were observed. The optimized sequences obtained by this method are provided in FIG. 6C and listed as SEQ ID NO: 28 and SEQ ID NO: 29. These sequences can then be further defined to more specifically determine the expression promoting regions contained therein. Therefore SEQ ID NO: 28 and SEQ ID NO: 29 or fragments thereof can be used in subsequent expression systems to promote the expression of the same or different protein.

Fv Expression Level Quantitation

The expression level of Fv fragments was determined by assaying cell free supernatants. Wildtype and purified mutant colonies were grown under expression conditions in CS broth as described above. Dilutions of antibody containing samples were incubated with radiolabelled metal-chelate. After incubation for one hour, the free, unbound metal chelate was separated from the antibody-bound metal chelate by centrifugation through a Millipore ultrafree filter (molecular wight cut-off of 10,000 MW, Millipore, Bedford, Mass.) Samples of the filtrated and the pre-filtration mixture were counted for radioactivity, yielding a "fraction bound". A standard curve of "fraction bound" versus known amounts of antibody was constructed. The amount of Fv in an unknown sample was determined from the standard curve. The results of the assay indicated that the mutants reproducibly expressed 10 times more active Fv fragment than the original construct.

The protein sequence of the antibody fragments in this example is not altered by wobble base mutagenesis. Therefore any difference in signal strength in the screening assay is due to differences in expression levels. However, the expression level may be affected by the mutation in several ways. The mRNA stability could be improved by the mutation. Similarly, initiation and translation from the ribosome may be improved. Further, protein expression is strongly influenced by the sequence of the first few codons following the ATG initiation codon (Bucheler et al., Gene 98:271–276, 1990. Therefore, wobble base mutagenesis can potentially influence polypeptide expression in a number of ways depending on where the mutagenic primers bind to nucleic acid and which random mutations are conferred upon the sequence.

EXAMPLE IV

In another preferred embodiment of this invention, EIPCR is used to create a promoter library for gene expression in *E. coli*.

Figure 7:
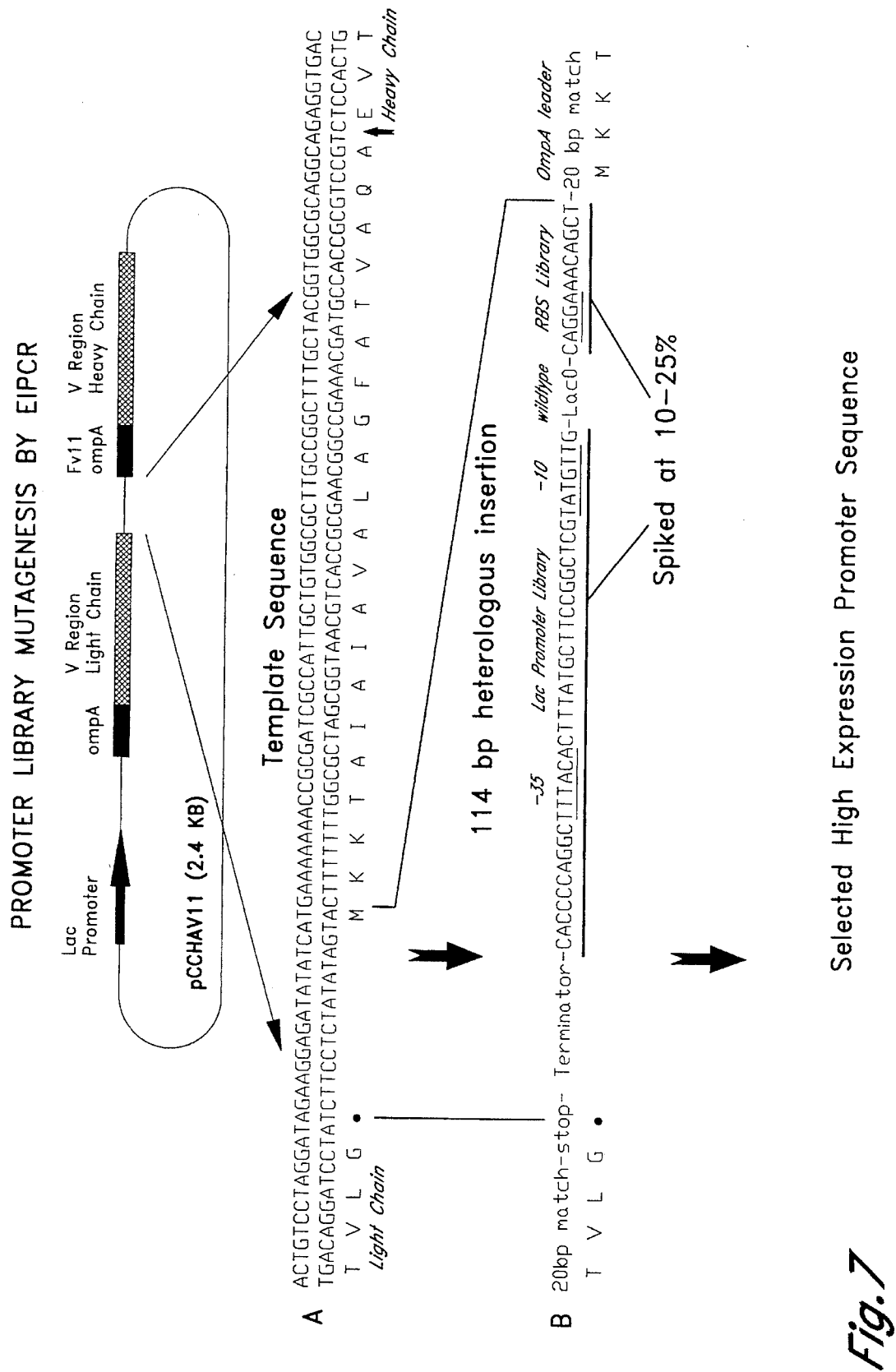
FIG. 7 is a schematic illustrating EIPCR promoter library mutagenesis. Line A is the template sequence. The underlined regions in Line B indicate the regions of variability in the library.

In this particular example of the preparation of a promoter library, Fv fragment expression of the anti-metal chelate antibody (CHA255) is optimized using a population of primers with variable sequences in the promoter region (FIG. 7).

Expression Vectors

In this example, the plasmid used is pCCHAV11, a 2.4 kb plasmid containing the Lac promoter followed by an OmpA leader sequence linked to the antibody light chain fragment sequence and followed by an optimized OmpA sequence linked to the antibody heavy chain fragment. Both antibody chain sequences are driven by a single Lac promoter. This optimized OmpA sequence (SEQ ID NO: 26) is derived from Example III. Plasmid pCCHAV11 is LacI negative, chloramphenicaol resistance gene positive with a Rop ColE 1 origin. In this example a second copy of the Lac promoter region is placed in front of the antibody heavy chain fragment sequence. The nucleic acid sequence is provided in FIG. 7A (ID SEQ NO: 30) and the inserted promoter sequence is provided in FIG. 7B and as ID SEQ NO: 33. The inserted region includes the Lac promoter library region followed by the wildtype Lac operator followed by the ribosome binding site. The sequence including the ribosome binding site is provided in ID SEQ NO: 34.

Oligonucleotide Synthesis

The primers used to create the recombinant promoter library are provided as ID SEQ NO: 31 and ID SEQ NO: 32. ID SEQ NO: 31 directed mutations to the ribosome binding site while ID SEQ NO: 32 directed changes to the Lac promoter region. In FIG. 7B the ribosome binding site, the −10 and the −35 regions of the Lac promoter are underlined and the sequence is provided as ID SEQ NO: 34 and ID SEQ NO: 33 respectively. The bold underlining in FIG. 7B corresponds to the primer regions in ID SEQ NO: 31 and ID SEQ NO: 32 that are underlined. The underlined portions are those positions along the primer that contain variability. The expected frequency of variability at each nucleotide position is derived from a mixture 75% of template nucleotide and 8.3% for each of the remaining three nucleotides. For example, in ID SEQ NO: 31, the first underlined position is a cytosine. The expected bias of the primer population at this position is: 75%:C, 8.3%:G, 8.3%:T, 8.3%:A. Libraries were created using primer populations based on ID SEQ NO: 31 and ID SEQ NO: 32. Other libraries were created using one biased primer population while the other member of the primer pair contained no variability. As an example, a recombinant library was created using ID SEQ NO: 31 to prepare a variable first primer pool, while the second primer corresponded exactly with ID SEQ NO: 32 and therefore contained no variability. The library generated from these primers contains mutated sequences at the ribosome binding site and a constant Lac promoter sequence. The oligonucleotides comprise a BsaI restriction endonuclease recognition site, a region of variability reflected in the underlined portion of ID SEQ NO: 31 and ID SEQ NO: 32, and a region complementary to the template.

PCR Amplification and Product Manipulation

Sequences were amplified using conditions outlined in Example III. Following amplification the nucleic acid was cleaved with BsaI and ligated. Nucleic acid was electroporated into *E. coli*.

Colony Screening Assay and Identification of Positive Clones

The screening assay is described in Example III. Colonies with increased levels of hapten binding are identified and colony purified. These colonies are expanded and analyzed for the presence of unintended mutations. Optimized promoter sequences are identified by sequencing the expression plasmids from positive colonies.

EXAMPLE V

In yet another preferred embodiment of this invention, EIPCR is employed to create a eukaryotic mutagenesis library. Similar to EIPCR in *E. coli*, any region of a eukaryotic vector can be modified. Eukaryotic expression vectors may be modified in regulatory regions or within translated regions of a particular gene. In this example, a retroviral expression vector pLN is used to generate a library of mutations within the ribosome binding site of the Neomycin resistance gene. The ribosome binding site, also known as a Kozak sequence (Kozak, M., Nuc. Acids. Res. 12(2):857–72, 1984 which is hereby incorporated by reference) is a highly conserved region in eukaryotic cells comprising the consensus sequence CCACCATG(G).

Expression Vector

The retroviral expression plasmid pLN was obtained from A. D. Miller and is described in a publication by Miller et al. (BioTechniques 7(9):980–990, 1989 which is hereby incorporated by reference). The vector contains two Moloney Murine Leukemia Virus (MoMuLV) long terminal repeats (LTR). Between the LTR regions is the Neomycin resistance gene (Neo$^r$). The Neo$^r$ ribosome binding site is targeted for library mutagenesis to confer increased resistance to G418 in the eukaryotic cell line NIH 3T3 (ATCC). The plasmid has a final size of 6 kb.

Oligonucleotide Synthesis

Oligonucleotides are prepared that are similar in design to those described for Example I above. The primers are designed to flank the Neo$^r$ ribosome binding site and are substantially complementary to both strands of DNA. A short (4–10 bp.) variable region is designed to overlap the ribosome binding site. Thus, the oligonucleotides contain a class IIS recognition site, the variable region, and a twenty base complementary region that anchors the oligonucleotides to the pLN plasmid.

Amplification Conditions

Reaction tubes are prepared for PCR in a final 100 ul. reaction volume. Reaction conditions are optimized from initial reaction conditions as outlined in Example III. Following PCR, the DNA is purified, cleaved with the desired class IIS restriction endonuclease, recircularized and ligated.

Isolation of Packaged Vector

Ligated product from the PCR reaction is electroporated into the helper virus packaging cell line PE501 obtained from A. D. Miller and described by Miller et al., supra. Mutated pLN is transiently packaged into retroviral particles using PE501. Cell supernatant containing viral particles is harvested from the packaging cell line and titered on virus susceptible NIH 3T3 cells (ATCC).

Selection and identification of Mutated Sequences

Colonies expressing mutations are selected with elevated levels of G418, preferably between 0.75–2.5 mg/ml These colonies are expanded, lysed, and if desired, the DNA is purified. The optimized promoter region is retrieved from the selected cells by PCR. This new Kozak sequence can then be reintroduced into pLN to verify that the new sequence confers elevated G418 resistance. The region is sequenced to identify the selected nucleic acid sequence. The results from this work permits the identification of sequences conferring increased G418 resistance and facilitates the identification of Kozak sequence requirements and the isolation of improved sequences that can be transferred to other constructs to improve the expression of other protein sequences.

It is additionally contemplated that this technology could be applied to any gene in combination with a selectable marker such as Neo$^r$. Therefore any gene or portion of a gene can be mutated and initially selected by its resistance to Neomycin. Subsequent selection will be required to distinguish the optimized mutation. Neomycin resistance is just one of a variety of selection systems useful for EIPCR library mutagenesis applications. For example, as a selection procedure, transfected cells can be screened by a Fluorescent Activated Cell Sorter (FACS) and positive colonies expanded from these cells for further analysis.

Thus, EIPCR library mutagenesis is a reliable and efficient method for obtaining optimized nucleic acid sequences. EIPCR reactions have an efficiency of 95% or better in reactions designed to measure the efficiency of mutagenesis. EIPCR library mutagenesis is generally applicable for de novo design or redesign of protein or nucleic acid sequences.

Although the invention has been described with reference to the above examples, it should be understood that various modifications can be made by those skilled in the art without departing from the invention. Accordingly, the invention is limited only by the following claims.

I claim:

1. A method for generating a recombinant mutagenesis library by introducing one or more changes within a predetermined region of a double stranded circular DNA sequence, comprising the steps of:
  (a) providing a first primer population and a second primer population, each of said primer populations comprising in a 5' to 3' orientation;
    (i) a class IIS recognition sequence, wherein said IIS recognition sequence is not complementary to the DNA sequence of the predetermined region of the double stranded circular DNA sequence to be mutagenized;
    (ii) a class IIS restriction enzyme cleavage site associated with said class IIS restriction enzyme recognition sequence;
    (iii) a region of variable base composition at predetermined positions in said primers; and
    (iv) a DNA sequence substantially complementary to said double stranded circular DNA sequence to allow hybridization thereto, wherein the DNA sequence immediately adjacent to said class IIS restriction enzyme cleavages site within said primer populations is not complementary to the DNA sequence of the predetermined region of the double stranded circular DNA sequence to be mutagenized;
  (b) denaturing said double stranded circular DNA sequence and hybridizing said first and second primer populations to opposite strands of said denatured double stranded circular DNA sequence to form a first pair of primer templates wherein said primers are oriented in opposite directions relative to one another and wherein said class IIS recognition sequence does not hybridize to the denatured double stranded circular DNA sequence;
  (c) performing extension, denaturing and hybridization steps of a polymerase chain reaction to generate at least one linear copy of said double stranded circular DNA sequence to incorporate said change directed by said primers;
  (d) cutting the linear copy of said double stranded circular DNA sequence of step (c) with a class IIS restriction enzyme to form a restricted linear DNA molecule containing said change to produce overhanging termini that are complementary to one another;

(e) ligating intramolecularly said overhanging termini of said linear DNA molecule to recircularize said linear copy of said double stranded circular DNA sequence containing said change; and (f) introducing said recircularized copies of double stranded DNA sequence into compatible host cells, wherein a recombinant mutagenesis library is generated.

2. The method of claim 1, wherein said restricted linear DNA molecule produced in step (d) contains only said change.

3. The method of claim 1, wherein at least steps (b) and (c) are repeated one or more times.

4. The method of claim 1 wherein step (d) further comprises treating said restricted linear DNA molecule with a polymerase under conditions which create blunt ends.

5. The method of claim 1, wherein said host cells are bacteria.

6. The method of claim 1, wherein said double stranded DNA encodes polypeptide.

7. The method of claim 6, additionally comprising the step of expressing said polypeptide encoded by the DNA of step (e).

8. The method of claim 1 wherein said host cells are eukaryotic.

9. The method of claim 6, wherein at least one of said changes is located within a polypeptide encoding region of the double stranded circular DNA.

10. The method of claim 6, wherein at least one of said changes is located within a regulatory region of said double stranded circular DNA.

11. The method of claim 1, wherein said double stranded DNA comprises a viral vector.

12. The method of claim 11, wherein said compatible host cells comprise a helper virus packaging cell line that directs the packaging of viral particles containing said viral vector.

13. The method of claim 12, further comprising the step of collecting said vital particles and infecting susceptible cells with said viral particles.

14. A method for improving polypeptide expression from a double stranded circular DNA sequence encoding polypeptide, comprising the steps of:

(a) measuring polypeptide expression from said double-stranded DNA in a compatible host cell;

(b) providing a first primer population and a second primer population, each of said primer populations comprising in a 5' to 3' orientation:

(i) a class IIS recognition sequence, wherein said class IIS recognition sequence is not complementary to a DNA sequence of a predetermined region of the double stranded circular DNA sequence to be mutagenized;

(ii) a class IIS restriction enzyme cleavage site associated with said class IIS restriction enzyme recognition sequence;

(iii) a region of variable base composition at predetermined positions along said primers; and (iv) a sequence substantially complementary to said double stranded circular DNA sequence to allow hybridization thereto, wherein the DNA sequence immediately adjacent to said class IIS restriction enzyme cleavage site within said primer populations is not complementary to the DNA sequence of the predetermined region of the double stranded circular DNA sequence to be mutagenized;

(c) denaturing said double stranded circular DNA sequence and hybridizing said first and second primer populations to opposite strands of said denatured double stranded circular DNA sequence to form a first pair of primer-templates wherein said primers are oriented in opposite directions relative to one another and wherein said class IIS recognition sequence does not hybridize to the denatured double stranded circular DNA sequence;

(d) performing extension, denaturating and hybridization steps of a polymerase chain reaction to generate at least one linear copy of said double stranded circular DNA sequence incorporating said change directed by said primers;

(e) cutting the linear copy of said double stranded circular DNA sequence of step (d) with a class IIS restriction enzyme to form a restricted linear DNA molecule containing said change to produce overhanging termini that are complementary to one another;

(f) ligating intramolecularly said overhanging termini of said linear DNA molecule to recircularize said linear copy of said double stranded circular DNA sequence containing said change;

(g) introducing said recircularized copies of double stranded DNA from step (f) into said host cells;

(h) measuring polypeptide expression from said modified DNA of step (g) in said cells; and (i) identifying cells with polypeptide expression greater than the polypeptide expression measured in step (a).

15. The method of claim 14 additionally comprising the step of obtaining modified DNA from said identified cells of step (i).

16. The method of claim 15, further comprising transferring the modified DNA sequence into another DNA sequence.

17. The method of claim 14, wherein said primers direct changes in a promoter sequence.

18. The method of claim 14, wherein said primers direct changes in a polypeptide sequence.

19. The method of claim 14, wherein said host cells are bacteria.

20. The method of claim 14, wherein said host cells are eukaryotic cells.

21. The method of claim 14, wherein said primers direct changes in a ribosome binding sequence.

22. The method of claim 14, wherein said primers direct alterations in a DNA coding for a leader sequence of said polypeptide.

23. The method of claim 22, wherein said leader sequence is the bacterial OmpA protein leader sequence or a fragment thereof.

24. The method of claim 22, wherein said leader sequence is linked to polynucleotide encoding light and heavy chain antibody fragments.

25. The method of claim 14, wherein the region of variable base composition contains a changed nucleotide relative to the double stranded circular DNA sequence and the changed nucleotide occurs in the third position of at least one codon in the double stranded circular DNA sequence.

26. An optimized OmpA protein leader consisting of DNA sequence:

5'ATGAAAAAAACTGCAATTGCGATTGCT-GTTGCTCTTGCTGGTTTCGCGACGGTAG-CACAGGCC 3'.

27. An optimized OmpA protein leader consisting of DNA sequence:

5'ATGAAAAAAACCGCGATCGCCATTGCT-GTGGCGCTTGCCGGCTTTGCTACGGTG-GCGCAGG3'.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:1:

AAATCTGGAG CCGGTGAGCG TGGGTCTCGC GGTATCATTG CAGCACTGGG GCCA    54

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ATTAGGTCTC GGTTCCCGCG GTATCATTGC AGCACT    36

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AATTGGTCTC GGAACCACGC TCACCGGCTC CAGAT    35

( 2 ) INFORMATION FOR SEQ ID NO:4:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:4:

AAATCTGGAG CCGGTGAGCG TGGTTCCCGC GGTATCATTG CAGCACTGGG GCCA　　　54

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGTCTCNNNN N　　　11

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GAAGACNNNN NN　　　12

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CTCTTCNNNN　　　10

( 2 ) INFORMATION FOR SEQ ID NO:8:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GAATGCN　　　7

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ACCTGCNNNN NNNN　　　14

( 2 ) INFORMATION FOR SEQ ID NO:10:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GGATCNNNNN         10

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GCAGCNNNNN NNNNNNN         17

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GTCTCNNNNN         10

( 2 ) INFORMATION FOR SEQ ID NO:13:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

ACTGGN         6

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GGATGNNNNN NNNNNNNN         18

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GACGCNNNNN NNNNN         15

( 2 ) INFORMATION FOR SEQ ID NO:16:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

GGTGANNNNN NNN     13

( 2 ) INFORMATION FOR SEQ ID NO:17:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GAAGANNNNN NNN     13

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GAGTCNNNNN     10

( 2 ) INFORMATION FOR SEQ ID NO:19:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GCATCNNNNN NNNN     14

( 2 ) INFORMATION FOR SEQ ID NO:20:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CCTCNNNNNN N     11

( 2 ) INFORMATION FOR SEQ ID NO:21:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:21:

AGGAACCAAA CTGACTGTCC TAGGATAGAA GGAGATATAT CATGAAAAAG ACAGCTGGCG     60

CAGGCCGAGG TGACCCTGGT GGAGTCTGGG     90

( 2 ) INFORMATION FOR SEQ ID NO:22:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

ATTAGAAGAC TACTCCNNNN NNNNNNNNN NNNNNNGAG GTGACCCTGG TGGAGTCT    5 8

( 2 ) INFORMATION FOR SEQ ID NO:23:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

AATTGAAGAC ATGGAGNNNN NNNNNNNNN NNNNNNTCCT AGGACAGTCA GTTTGGTT    5 8

( 2 ) INFORMATION FOR SEQ ID NO:24:

( i ) SEQUENCE CHARACTERISTICS:
    ( A ) LENGTH: 94 base pairs
    ( B ) TYPE: nucleic acid
    ( C ) STRANDEDNESS: double
    ( D ) TOPOLOGY: circular ( i i ) MOLECULE TYPE: cDNA ( i x ) FEATURE:
    ( A ) NAME/KEY: CDS
    ( B ) LOCATION: 2..94

( x i ) SEQUENCE DESCRIPTION: SEQ ID NO:24:

```
A  GGA  ACC  AAA  CTG  ACT  GTC  CTA  GGA  CGG  AAA  TCG  GGG  CGG  TCT  ACC        4 6
   Gly  Thr  Lys  Leu  Thr  Val  Leu  Gly  Arg  Lys  Ser  Gly  Arg  Ser  Thr
   1              5                        10                       15

TCC  CCT  CTC  CCA  ATA  AAA  TTA  GGG  GAG  GTG  ACC  CTG  GTG  GAG  TCT  GGG      9 4
Ser  Pro  Leu  Pro  Ile  Lys  Leu  Gly  Glu  Val  Thr  Leu  Val  Glu  Ser  Gly
                    20                       25                       30
```

( 2 ) INFORMATION FOR SEQ ID NO:25:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: protein ( x i ) SEQUENCE DESCRIPTION: SEQ ID NO:25:

```
Gly  Thr  Lys  Leu  Thr  Val  Leu  Gly  Arg  Lys  Ser  Gly  Arg  Ser  Thr  Ser
1              5                        10                       15

Pro  Leu  Pro  Ile  Lys  Leu  Gly  Glu  Val  Thr  Leu  Val  Glu  Ser  Gly
               20                       25                       30
```

( 2 ) INFORMATION FOR SEQ ID NO:26:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

TCTATAGGTC TCTTTGCNGT NGCNCTNGCN GGNTTYGCNA CNGTNGCNCA RGCNGAGGTG    6 0

ACCCTGGTGG AG                                                                                    72

( 2 ) INFORMATION FOR SEQ ID NO:27:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

TATTAAGGTC TCAGCAATNG CRATNGCNGT YTTYTTCATG ATATATCTCC TTCTAT                                    56

( 2 ) INFORMATION FOR SEQ ID NO:28:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:28:

```
ATG  AAA  AAA  ACC  GCG  ATC  GCC  ATT  GCT  GTG  GCG  CTT  GCC                                 39
MET  LYS  LYS  THR  ALA  ILE  ALA  ILE  ALA  VAL  ALA  LEU  ALA
 1              5                        10

GGC  TTT  GCT  ACG  GTG  GCG  CAG  GCA                                                           63
GLY  PHE  ALA  THR  VAL  ALA  GLN  ALA
        15                   20
```

( 2 ) INFORMATION FOR SEQ ID NO:29:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: circular ( i i ) MOLECULE TYPE: cDNA ( x i ) SEQUENCE DESCRIPTION: SEQ ID NO:29:

```
ATG  AAA  AAA  ACT  GCA  ATT  GCG  ATT  GCT  GTT  GCT  CTT  GCT                                 39
MET  LYS  LYS  THR  ALA  ILE  ALA  ILE  ALA  VAL  ALA  LEU  ALA
 1              5                        10

GGT  TTC  GCG  ACG  GTA  GCA  CAG  GCC                                                           63
GLY  PHE  ALA  THR  VAL  ALA  GLN  ALA
        15                   20
```

( 2 ) INFORMATION FOR SEQ ID NO:30:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

AAGGAGATAT ATC                                                                                   13

( 2 ) INFORMATION FOR SEQ ID NO:31:

( i ) SEQUENCE CHARACTERISTICS:
        ( A ) LENGTH: 85 base pairs
        ( B ) TYPE: nucleic acid
        ( C ) STRANDEDNESS: single (D) TOPOLOGY: linear (xi) SEQUENCE DESCRIPTION: SEQ ID NO:31:

AACTATTGGT CTCAGTGGAA TTGTGAGCGG ATAACAATTT CACACAGGAA ACAGCTATGA    60

AAAAAACCGC GATCGCCATT GCTGT    85

(2) INFORMATION FOR SEQ ID NO:32:

(i) SEQUENCE CHARACTERISTICS:
(A) LENGTH: 109 base pairs
(B) TYPE: nucleic acid
(C) STRANDEDNESS: single
(D) TOPOLOGY: linear (xi) SEQUENCE DESCRIPTION: SEQ ID NO:32:

ATCATTAGGT CTCACCACAC AACATACGAG CCGGAAGCAT AAAGTGTAAA GCCTGGGGTG    60

AAAAAAAAAG GCTCCAAAAG GAGCCTTTCT ATCCTAGGAC AGTCAGTTT    109

(2) INFORMATION FOR SEQ ID NO:33:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:33:

CACCCCAGGC TTTACACTTT ATGCTTCCGG CTCGTATGTT G    41

(2) INFORMATION FOR SEQ ID NO:34:

(i) SEQUENCE CHARACTERISTICS:
(A) LENGTH: 12 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:34:

CAGGAAACAG CT    12